US005854413A

United States Patent [19]
Hawkins et al.

[11] Patent Number: 5,854,413
[45] Date of Patent: Dec. 29, 1998

[54] SYNAPTOGYRIN HOMOLOG

[75] Inventors: Phillip R. Hawkins, Mountain View; Susan G. Stuart, Montara; Lynn E. Murry, Portola Valley, all of Calif.

[73] Assignee: Incyte Pharmaceuticals, Inc., Palo Alto, Calif.

[21] Appl. No.: 700,637

[22] Filed: Apr. 30, 1996

[51] Int. Cl.$^6$ .............................. C12P 21/02; C12Q 1/68; C07H 21/04; C12N 5/10
[52] U.S. Cl. ........................... 536/23.5; 435/6; 435/69.1; 435/172.3; 435/325; 435/320.1
[58] Field of Search ................................ 536/23.5; 435/6, 435/332.5, 320.1, 325, 69.1, 172.3

[56] References Cited

PUBLICATIONS

Stenius, K et al. J. Cell Biol. 131(6.2): 1801–1809, Dec. 1995.
Sudhof, TC et al. Nuc. Acid Res. 15: 9607, Nov. 1987.
Strobach, RS et al. Mod. Pathol. 3(4): 488–493, Jul. 1990.
Ushiyama, T et al. J. Rheumatol. 22(3): 421–426, Mar. 1995.
Baumert, M. et al., "P29: A Novel Tyrosine–phosphorylated Membrane Protein Present In Small Clear Vesicles of Neurons and Endocrine Cells" *J. Cell Biol.*, 1285–94 (1990).
Ralston, E. et al., "Expression of the Synaptic Vesicle Proteins VAMPs/Synaptobrevins 1 and 2 in Non–neural Tissues" *Biol. Chem.*, 269:15403–6 (1994).
Baumert, M. et al., "Synaptobrevin: an integral membrane protein of 18 000 daltons present in small synaptic vesicles of rat brain" *Embo. J.*, 8:379–84 (1989).
McMahon, HT et al., "Cellubrevin is a ubiquitous tetanus–toxin substrate homologous to a putative synaptic vesicle fusion protein" *Nature* 364:346–349 (1993).
Galli, T. et al., "Tetanus Toxin–mediated Cleavage of Cellubrevin Impairs Exocytosis of Transferrin Receptor–Containing Vesicles in CHO Cells" *J. Cell Biol.*, 125:1015–24 (1994).
Link, E. et al., "Cleavage of Cellubrevin by Tetanus Toxin Does Not Affect Fusion of Early Endosomes" *J. Biol. Chem.*, 268:18423–6 (1993).
Bark, I.C. et al., "Regulated vesicular fusion in neurons: Snapping together the details" *Proc. Natl. Acad. Sci.*, 91:4621–4624 (1994).

*Primary Examiner*—David Saunders
*Assistant Examiner*—F. Pierre VanderVegt
*Attorney, Agent, or Firm*—Lucy J. Billings; Incyte Pharmaceuticals, Inc.

[57] ABSTRACT

The present invention provides a polynucleotide (snpg) initially isolated from a colon cDNA library which identifies and encodes a novel human synaptogyrin homolog (SNPG). The invention provides for genetically engineered expression vectors and host cells comprising the nucleic acid sequence encoding SNPG. The invention also provides for the use of SNPG in the membrane of a vesicle containing a chemical or biological therapeutic composition for the treatment of disease, and for the therapeutic use of antisense molecules, antibodies, antagonists or inhibitors in the treatment of conditions or diseases associated with the abnormal or excess expression of SNPG. The invention also describes diagnostic assays which utilize diagnostic compositions comprising the polynucleotide, fragments or the complement thereof, which hybridize with the genomic sequence or the transcript of snpg, or anti–SNPG antibodies which specifically bind to the polypeptide, SNPG.

6 Claims, 14 Drawing Sheets

```
                                                                              9                 18         27              36              45           54
5' ATG GAG AGC GGG GCC TAC GGC GCC AAG GCG GGC TCC TTC GAC CTG CGG
   M   E   S   G   A   Y   G   A   K   A   G   S   F   D   L   R
     63              72          81              90          99         108
   CGC TTC CTG ACG CAG CCG CAG GTG GTG GCG CGC GCC GTG TGC TTC GCC
   R   F   L   T   Q   P   Q   V   V   A   R   A   V   C   F   A
   117             126         135             144         153         162
   TTG ATC GTG TTC TCC TGC ATC TAT GGT GAG GGC TAC AGC AAT GCC CAC GAG TCT
   L   I   V   F   S   C   I   Y   G   E   G   Y   S   N   A   H   E   S
   171             180         189             198         207         216
   AAG CAG ATG TAC TGC GTG TTC AAC CGC AAC GAG GAT GCC TGC CGC TAT GGC AGT
   K   Q   M   Y   C   V   F   N   R   N   E   D   A   C   R   Y   G   S
   225             234         243             252         261         270
   GCC ATC GGG GTG CTG GCC TTC CTG GCC TCG ACT GAC CGC TTC TTG GTG GTC GAC GCG
   A   I   G   V   L   A   F   L   A   S   T   D   R   F   L   V   V   D   A
   279             288         297             306         315         324
   TAT TTC CCC CAG ATC AGC AAC GCC ACT GAC CGC AAG TAC CTG GTC ATT GGT GAC
   Y   F   P   Q   I   S   N   A   T   D   R   K   Y   L   V   I   G   D
   333             342         351             360         369         378
   CTG CTC TTC TCA GCT CTC TGG ACC TTG CTG TTT GTT GGT TTC TGC TTC CTC
   L   L   F   S   A   L   W   T   L   L   F   V   G   F   C   F   L
```

FIGURE 1A

```
ACC AAC CAG TGG GCA ACC AAC CCG AAG GAC GTC CTG GTG GGG GCC GAC TCT
 T   N   Q   W   A   T   N   P   K   D   V   L   V   G   A   D   S
387         396         405         414         423         432

GTG AGG GCA GCC ATC ACC TTC TTT TCC ATC TTC TCC TGG GGT GTG CTG
 V   R   A   A   I   T   F   F   S   I   F   S   W   G   V   L
441         450         459         468         477         486

GCC TCC CTG GCC TAC CAG CGC TAC AAG GCT GGC GTG GAC GAC TTC ATC CAG AAT
 A   S   L   A   Y   Q   R   Y   K   A   G   V   D   D   F   I   Q   N
495         504         513         522         531         540

TAC GTT GAC CCC ACT CCG GAC CCC AAC ACT GCC TAC GCC TCC TAC CCA GGT GCA
 Y   V   D   P   T   P   D   P   N   T   A   Y   A   S   Y   P   G   A
549         558         567         576         585         594

TCT GTG GAC AAC TAC CAA CAG CCA CCC TTC ACC CAG AAC GCG GAG ACC ACC GAG
 S   V   D   N   Y   Q   Q   P   P   F   T   Q   N   A   E   T   T   E
603         612         621         630         639         648

GGC TAC CAG CCG CCC CCT GTG TAC TGA  3'
 G   Y   Q   P   P   P   V   Y   *
657         666         675
```

```
1  CAGTCGTGTAATACGACTCACTATAGGGAAAGCTGGTTAC  775426
1  ---------------------------------------  392250
1  ---------------------------------------  476266
1  ---------------------------------------  608493
1  ---------------------------------------  693335
1  ---------------------------------------  695983
1  ---------------------------------------  754306
1  ---------------------------------------  809604
1  --------------------------------------C  868416

41 GCCTGCAGGTACCGGTCCGGAATTCCCGGTCGACCCACG  775426
41 --------------------------------------  392250
41 --------------------------------------  476266
41 --------------------------------------  608493
41 --------------------------------------  693335
41 --------------------------------------  695983
41 --------------------------------------  754306
41 --------------------------------------  809604
42 --------------------------------------  868416

81 CGTCCGGCCGGCAGCCGGCACGGCGACGGCGACATGGAGAGCGG  775426
81 --------------------------------------------  392250
81 --CCG------G-------------------------AGCGG  476266
81 --------G-----------------------------AGCGG  608493
81 -----------------------------------AGAGCGG  693335
81 ---------------A---------------------AGAGCGG  695983
81 --GCGGCAG---------------------------AGAGCGG  754306
81 -------------------------------AGAGGAGCGG  809604
82 GCGGCAG------------------GACATGGAGAGCGG  868416
```

FIGURE 2B

```
121 GGCCTACGGCGCGGCCCAAAGGCGGGCCTCCTTCGACCTG 775426
  1 - - - - - - - - CGGCCCAAAGGCGGGCTCCCTTCGACCTG 392250
 27 GGCCTACGGCGCGGCCCAAAGGCGGGCCTCCTTCGACCTG 476266
  6 GGCCT - - CGGCGCGGCCCAAAGGCGGGCTCCCTTCGACCTG 608493
  4 - - - - - - - - CGGCCCAAAGGCGGGCTCCCTTCGACCTG 693335
  1 - - - - - - - CGGCCCAAAGGCGGGNTNCCTTCGACCTN 695983
  9 - - - - - - - GGCGCGGCCCAAAGGCGGGCTCCCTTCGACCTG 754306
 35 GGCCTACGGCGCGGCCCAAAGGCGGGCCTCCTTCGACCTG 809604
 16 GGCCTACGGCGCGGCCCAAAGGCGGGCTCCCTTCGACCTG 868416

161 CGGGCGGCGACTGATTTCCTTTGGCCCAAGCAGGTGGGCCCG 775426
 31 CGGGCGGCGACTGATTTCCTTTGGCCNAAGCAGGTGGGCCCG 392250
 67 CGGGCGGCGACTGATTTCCTNTGGCCCAAGCAGGTGGGCCCG 476266
 46 CGGGCGGCGACTGATTTCCTTTGGCCNAAGCAGGTGGGCCCG 608493
 33 CGGGCGGCGACTGATTTCCTTTGGCCCAAGCAG-TGGGCCCG 693335
 34 CGGGCGGCGACTGATTTCCTTTGGCCCAANCANGTGGGCCCG 695983
 49 CGGGCGGCGACTGATTTCCTTTGGCCCAAGCAG-TGGGCCCG 754306
 75 CGGGCGGCGACTGATTTCCTNTGGCCNAAGCAG-TGGGCCCG 809604
 56 CGGGCGGCGACTGATTTCCTTTGGCCCAAGCAGGTGGGCCCG 868416

201 TGTGCTTGGTTCTTTCGGCCCTTTGATTCGGTGTTTCTTCCCTGCCATCTA 775426
 71 TGTGCTTGGTTCTTTCGGNCCTTTGATTCGGTGTTTCTTCCCTGCCATCTA 392250
107 TGTGCTTGGTTCTTTCGGCCCTTTGATTCGGTGTTTCTTCCCTGCCATCTA 476266
 86 TGTGCTTGGTNCTTTCGGCCCTTTGATTCGGTGTTTCTTCCCTGCCATCTA 608493
 72 TGTGCTTGGTTCTTTCGGCCCTTTGATTCGGTGTTTCTTCCCTGCCATCTA 693335
 74 TGTGCTTGGTTCTTTCGGCCCTTTGATTCGGTGTNTCTTCCCTGCCATNTA 695983
 88 TGTGCTTGGTTCTTTCGGCCCTTTGATTCGGTGTTTCTTCCCTGCCATCTA 754306
114 TGTGCTTGGTTCTTTCGGCCCTTTGATTCGGTGTTTCTTCCCTGCCATCTA 809604
 96 TGTGCTTGNTTCTTTCGGNCCTTTGATTCGGTGTTTCTTCCCTGCCATCTA 868416
```

```
481 CTTCCTCACCAACCAGTGGGCAGTCAACCCGAAGGAC  775426
232  ------------------------------------  392250
272  ------------------------------------  476266
265  ------------------------------------  608493
192  ------------------------------------  693335
220  ------------------------------------  695983
230  ------------------------------------  754306
296  ------------------------------------  809604
269  ------------------------------------  868416

521 GTGCTGGTGGGGCCGACTCTGTGAGGGCAGCCATCACCT  775426
232  ------------------------------------  392250
272  ------------------------------------  476266
265  ------------------------------------  608493
192  ------------------------------------  693335
220  ------------------------------------  695983
230  ------------------------------------  754306
296  ------------------------------------  809604
269  ------------------------------------  868416

561 TCAGCTTCTTTTCCATCTTCTCCTGGGTGTGCTGGCCTC  775426
232  ------------------------------------  392250
272  ------------------------------------  476266
265  ------------------------------------  608493
192  ------------------------------------  693335
220  ------------------------------------  695983
230  ------------------------------------  754306
296  ------------------------------------  809604
269  ------------------------------------  868416
```

```
721 ACAGCCACCCTTCACCCAGAACGCGGAGACCACCGAGGGC  775426
232                                          392250
272                                          476266
265                                          608493
192                                          693335
220                                          695983
230                                          754306
296                                          809604
277 ----------------AGAACGCA-----TNCCGAAGAC  868416

761 TACCAGCCGCCCCCTGTGTACTGAGCGGCGGTTAGCGTGG  775426
232                                          392250
272                                          476266
265                                          608493
192                                          693335
220                                          695983
230                                          754306
296                                          809604
295 T-------GNATTGNNC-----------------------  868416

801 GAAGGGGGACAGAGAGGGCCCCTTCCCCTCTGCCCTGGACTT 775426
232                                            392250
272                                            476266
265                                            608493
192                                            693335
220                                            695983
230                                            754306
296                                            809604
305 ------------------------------TNTTTTAG--TT 868416
```

```
961 CTGTGCCCA
232
272
265
192
220
230
296
339
```

SYNAPTOGYRIN HOMOLOG

FIELD OF THE INVENTION

The present invention relates to nucleic acid and amino acid sequences of a novel synaptogyrin homolog from colon and to the use of these sequences in the diagnosis, study, prevention and treatment of disease.

BACKGROUND OF THE INVENTION

Synaptogyrin is a 25.9 kD synaptic vesicle-associated membrane protein (VAMPs) from rat. The protein resides on post-Golgi compartments, has four membrane spanning domains, and displays both NH2 and COOH termini on the cytoplasmic side of the membrane (Stenius K. et al. (1995) Jour Cell Biol 131:1801–09). It is phosphorylated on tyrosine residues, and has no evidence of N-linked glycosylation. Cytological investigations of the intracellular, vesicular trafficking pathways indicate that synaptogyrin displays punctate staining similar to that of transferrin, and that synaptogyrin is important in membrane recycling.

Synaptogyrin was reported to be uniformly distributed in the nervous system (Baumert M. et al (1990) J Cell Biol 110:1285–94) and is related to the multigene families of vesicular trafficking proteins which include cellubrevins, synaptobrevins and synaptophysin. These proteins are associated with the membranes of the synaptic vesicles, inclusion bodies which store neurotransmitters. The cDNA has been cloned from thymus and liver tissues; and the transcript has been reported in brain and nonneuronal tissues such as heart, spleen, liver, lung, skeletal muscle, kidney and testes.

Synaptobrevin, an integral membrane protein of 18 kDA (Ralston E. et al (1994) J Biol Chem 269:15403–6), was first discovered in rat brain (Baumert M. et al (1989) Embo J 8:379–84) and initially thought to be limited to neuronal cells. Synaptobrevin is involved in the movement of vesicles from the plasmalemma of one cell, across the synapse, to the plasma membrane of the receptive neuron. Synaptophysin appears to regulate the ability of synaptobrevin to enter the presynaptic fusion complex, and cleavage of the synaptobrevin molecule by clostridial neurotoxins prevents neurotransmitter release.

Cellubrevins are 16 kDa proteins first found and investigated in rat cells and tissues (McMahon H. T. et al (1993) Nature 364:346–9). In vitro studies of various cellular membranes (Galli T. et al (1994) J Cell Biol 125:1015–24; Link E. et al (1993) J Biol Chem 268:18423–6) have shown that the cellubrevins are widely distributed. They appear to participate in axon extension via exocytosis during development, in the release of neurotransmitters and modulatory peptides, and in endocytosis.

As mentioned for synaptobrevin above, cellubrevins are sensitive to selective proteolysis by metalloendoproteases such as the zinc endoprotease which comprises the light chain of tetanus toxin. Experiments have shown that endosome fusion may continue even after specific cellubrevin cleavage through temperature- and ATP-dependent docking and fusion processes involving N-ethylmaleimide-sensitive fusion proteins (NSF) and small, soluble attachment proteins (SNAP).

VAMPs are associated with particular cell types, participate in both intracellular and extracellular pathways, and appear to vary in their abundance and specificity. Elucidation of the interactions of novel VAMPs with docking proteins such as syntaxin and SNAPs of the plasmalemma or the core fusion proteins such as NSF and the synaptotagmins (Bark I. C. and Wilson M. C. (1994) Proc Natl Acad Sci 91:4621–4624) provide means for the regulation of vesicular trafficking in normal as well as acute and chronic disease situations.

SUMMARY

The present invention relates to a novel synaptogyrin homolog initially identified among the partial cDNAs from a colon library and to the use of the nucleic acid and amino acid sequences in the study, diagnosis, prevention and treatment of disease. The synaptogyrin of the present invention was first identified within Incyte Clone 775426 through a computer generated search for amino acid sequence alignments. The nucleic acid sequence, SEQ ID NO: 1, disclosed herein and designated in lower case, snpg, encodes the amino acid sequence, SEQ ID NO: 2, designated in upper case, SNPG. The present invention is based, in part, on the chemical and structural homology between SNPG and rat synaptogyrin (GenBank GI 1072118; Stenius K. et al (1995) J Cell Biol 131:1801–9).

Based on homology to known rat synaptogyrin and human synaptophysin, the synaptogyrin disclosed herein appears to represent a new family of VAMPs. Since these proteins are more numerous and widely distributed than initially recognized, their expression and subcellular localization provides a means to intercede in diseases associated with the cell types and tissues discussed herein.

SNPG is 224 amino acids long and has potential N-linked glycosylation site at $N_{97}$. It contains two sets of cysteine residues, $C_{32}$ to $C_{42}$ which appear to lie within the first membrane spanning domain and, $C_{59}$ to $C_{68}$ which align with the set of cysteine residues in rat synaptobrevin which has been predicted to form an intramolecular loop. SNPG has approximately 49% amino acid identity to rat synaptogyrin. The nucleic acid sequence, oligonucleotides, fragments, portions or antisense molecules thereof, may be used in diagnostic assays of body fluids or biopsied tissues to detect expression of snpg. For example, snpg sequences designed from the coding, or signal, sequences of Incyte Clones 392250, 476266, 608493, 693335, 695983, 754306, 809604 and 868416 (SEQ ID NOs: 5–12) can be used to detect the presence of the mRNA transcripts in a patient or to monitor the decrease in transcripts during treatment.

The nucleic acid sequence also provides for the design of antisense molecules useful in diminishing or eliminating expression of the genomic nucleotide sequence in individuals in which reducing or redirecting vesicular trafficking ameliorates disease or the symptoms of disease. The present invention also relates, in part, to the inclusion of the polynucleotide in an expression vector which can be used to transform host cells or organisms. Such transgenic hosts are useful for production of SNPG.

The invention further provides diagnostic kits for the detection of naturally occurring SNPG. It provides for the use of purified SNPG to produce antibodies or to use in the identification of antagonists or inhibitors which specifically bind SNPG. These antagonists or inhibitors can be delivered in the vascular system, lymph or cerebrospinal fluid to bind with SNPG and prevent vesicle targeting and/or membrane docking. Anti-SNPG antibodies are useful in an analogous manner and to monitor SNPG in membrane preparations from biopsied tissues where SNPG is expressed.

When SNPG is inserted into artificial vesicle membranes or liposomes, it is useful as an address label. The ability to insert a VAMP into a vesicle membrane and target the vesicle to a particular cell or tissue provides a means to deliver other chemical or biological therapeutics to diseased cells and tissues to control or ameliorate such diseases and their symptoms.

The invention comprises pharmaceutical compositions encompassing vesicles containing the inserted polypeptide as well as antisense molecules capable of disrupting expression of the native gene, and antibodies, antagonists or inhibitors of the disclosed peptide. These compositions are useful for the prevention or treatment of conditions such as AIDS; allergies including hay fever, asthma, and urticaria (hives); autoimmune hemolytic anemia; cancers, leukemias or lymphomas; ulcerative colitis; juvenile diabetes mellitus; proliferative glomerulonephritis; inflammatory bowel disease; multiple sclerosis; myasthenia gravis; rheumatoid and osteoarthritis; scleroderma; Chediak-Higashi and Sjogren's syndromes; systemic lupus erythematosus; thyroiditis; toxic shock syndrome; traumatic tissue damage; viral, bacterial, fungal and protozoal infections; and other physiologic/pathologic problems associated with induced, and otherwise abnormal, vesicular trafficking.

DESCRIPTION OF THE FIGURES

FIGS. 1A and 1b display the nucleic acid sequence (SEQ ID NO:1) and deduced amino acid sequence (SEQ ID NO:2) of the novel synaptogyrin, SNPG, from human colon (COLNNOT05). The alignment of the nucleic acid and amino acid sequences was produced using MACDNASIS software (Hitachi Software Engineering Co Ltd).

FIGS. 2A, 2B, 2C, 2D, 2E, 2F, 2G, 2H and 2I show the nucleic acid sequence alignment of Incyte Clone 775426 (SEQ ID NO:1) with eight other partial cDNAs, Incyte Clones 392250 (SEQ ID NO:5), from T cells in mixed lymphocyte reaction, 476266 (SEQ ID NO:6) from macrophages in mixed lymphocyte reaction; 608493 (SEQ ID NO:7) from colon; 693335 (SEQ ID NO:8) from lung tumor; 695983 (SEQ ID NO:9) from rheumatoid synovium; 754306 (SEQ ID NO:10) from brain tumor; 809604 (SEQ ID NO:11) from lung; and 868416 (SEQ ID NO:12) from asthmatic lung. Sequences were aligned using the multisequence alignment program of DNASTAR software (DNAStar Inc, Madison Wis.).

FIGS. 3A and 3B show the amino acid sequence alignment between SNPG (SEQ ID NO:2), rat synaptogyrin (GI 1072118 (SEQ ID NO:3); Stenius K. et al. (1995) J Cell Biol 131:1801–9) and human synaptophysin (GI 899301 (SEQ ID NO:4); Sudhof T. C. et al. (1987) Nuc Acids Res 15:9607). Sequences were aligned using the multisequence alignment program of DNASTAR software.

DETAILED DESCRIPTION OF THE INVENTION

Figure 4:
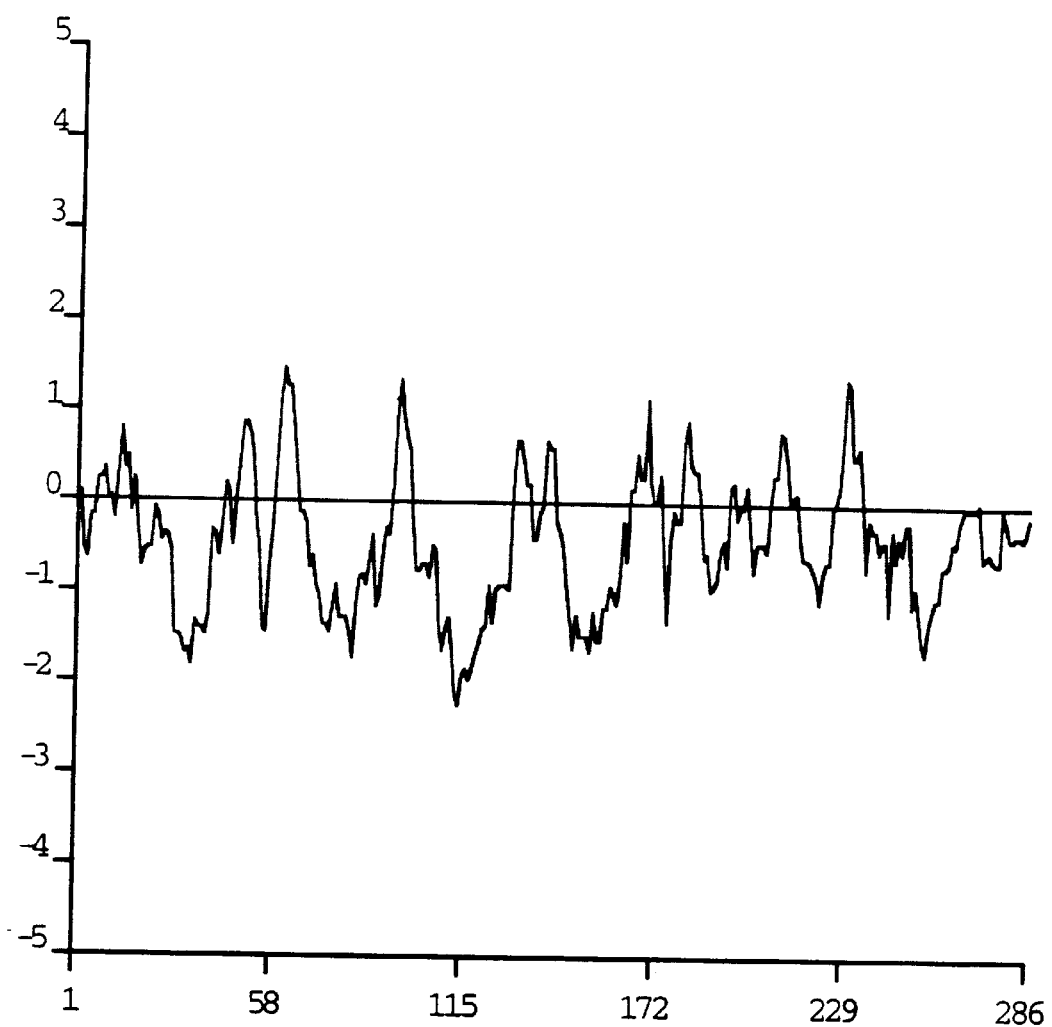
FIG. 4 shows the four membrane spanning domains of SNPG. The X axis reflects amino acid position, and the negative Y axis, hydrophobicity (MACDNASIS software).

The present invention relates to a novel synaptogyrin, the partial nucleic acid sequence for which was initially identified in Incyte Clone 775426 from a colon cDNA library (COLNNOT05) prepared from the colon removed from a 40-year-old Caucasian male with Crohn's disease and to the use of the polynucleotide (lower case, snpg) and polypeptide (upper case, SNPG) shown in FIGS. 1A and 1B in the study, diagnosis, prevention and treatment of disease.

SNPG is 224 amino acids long and has approximately 49% amino acid identity to rat synaptogyrin (GenBank GI 1072118; Stenius K. et al (1995) J Cell Biol 131:1801–9). SNPG has a potential N-linked glycosylation site at $N_{97}$. It contains two sets of cysteine residues, $C_{32}$ to $C_{42}$, which appear to lie within the first membrane spanning domain and, $C_{59}$ to $C_{68}$, which align with the set of cysteine residues in rat synaptobrevin predicted to form an intramolecular loop.

Figure 2C:
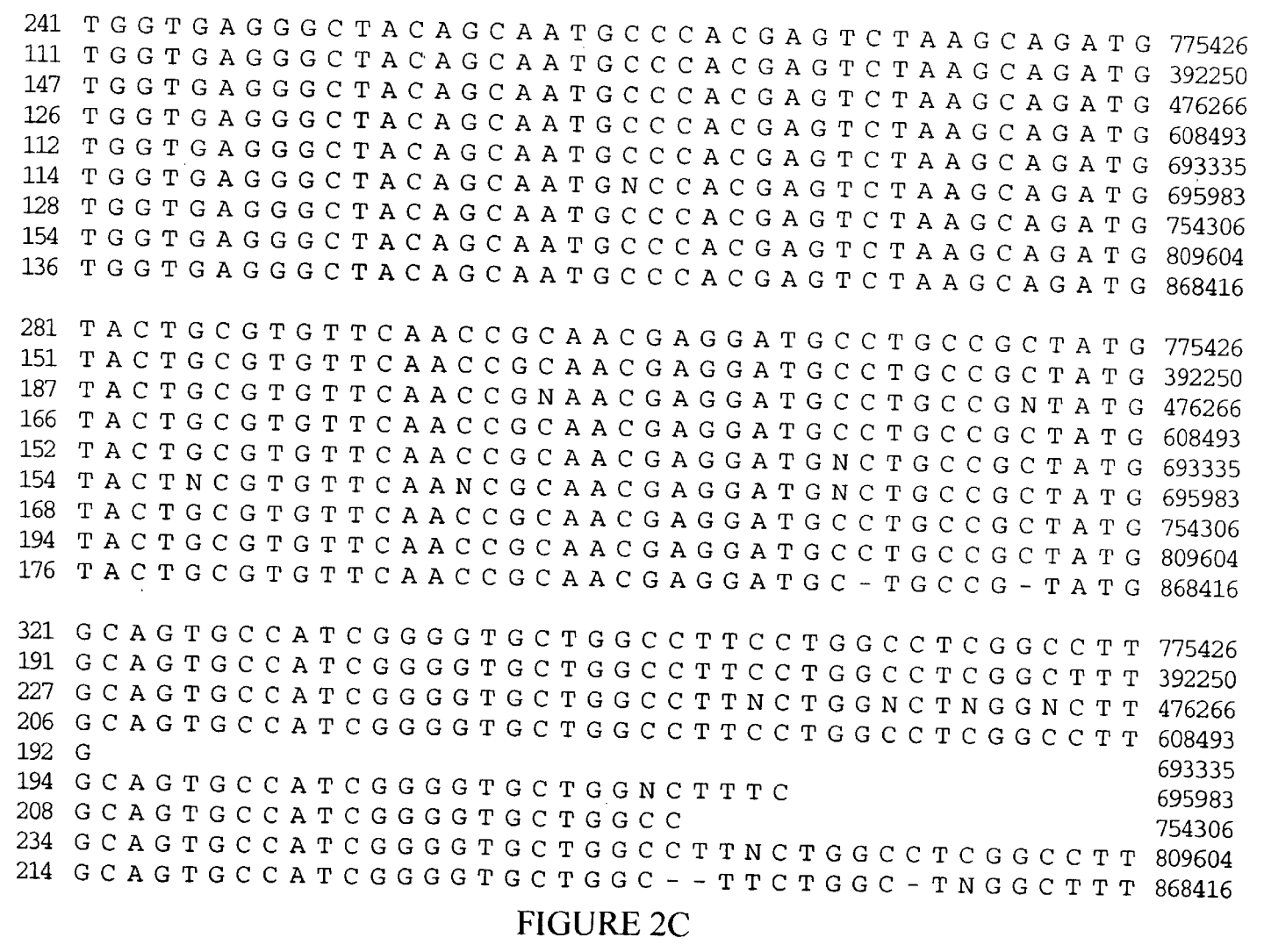

The present invention provides a nucleotide sequence (SEQ ID NO:1) which uniquely identifies a novel human synaptogyrin homolog. SNPG transcripts (SEQ ID Nos:5–11) were specifically expressed in the colon removed from a 75-year-old Caucasian male with a colon tumor (COLNNOT01) and lung removed from a 2-year-old Hispanic male (LUNGNOT04) and has been associated with inflamed or diseased cells or tissues such as T cells in mixed lymphocyte reaction (TMLR2DT01), macrophages in mixed lymphocyte reaction (MMLR2DT01), lung tumor (LUNGTUT02), rheumatoid synovium (SYNORAT03), brain tumor (BRAITUT02), and asthmatic lung (LUNGAST01). FIGS. 2A, 2B, 2C, 2D, 2E, 2F, 2G, 2H and 2I show the alignment between SEQ ID NO:1 and SEQ ID NOs: 5–12 identified from these eight different libraries.

The nucleic acid (snpg), polypeptide (SNPG) and antibodies to SNPG are useful in investigations of and interventions in vesicular trafficking and physiologic or pathologic processes demonstrated in these tissues. SNPG can be used to detect the presence of the mRNA transcripts in a patient and to monitor the change in transcript levels during treatment of Crohn's disease, chronic diseases such as rheumatoid arthritis and asthma, cancers or tumors of the colon, lung and brain.

The nucleic acid sequence also provides for the design of antisense molecules useful in diminishing or eliminating expression of the genomic nucleotide sequence in individuals in which reducing or redirecting vesicular trafficking ameliorates disease or the symptoms of disease. The present invention also relates, in part, to the inclusion of the polynucleotide in an expression vector which can be used to transform host cells or organisms. Such transgenic hosts are useful for production of SNPG.

The invention further provides diagnostic kits for the detection of naturally occurring SNPG. It provides for the use of purified SNPG to produce antibodies or to use in the identification of antagonists or inhibitors which specifically bind SNPG. These antagonists or inhibitors can be delivered into the vascular system, lymph or cerebrospinal fluid to bind with SNPG and prevent vesicle targeting and/or membrane docking. Anti-SNPG antibodies are also useful to inhibit vesicle docking and as a diagnostic composition to investigate or monitor SNPG-containing vesicle formation and trafficking in biopsied ectodermal or neural tissues.

When SNPG is inserted into artificial vesicle membranes or liposomes, it is useful as an address label. The ability to insert a VAMP into a vesicle membrane and target the vesicle to a particular cell or tissue provides a means to deliver other chemical or biological therapeutics to diseased cells and tissues to control or ameliorate such diseases and their symptoms.

The invention comprises pharmaceutical compositions encompassing vesicles containing the inserted polypeptide as well as antisense molecules capable of disrupting expression of the native gene, and antibodies, antagonists or inhibitors of the peptide. These compositions are useful for the prevention or treatment of conditions such as AIDS; allergies including hay fever, asthma, and urticaria (hives); autoimmune hemolytic anemia; cancers, leukemias or lymphomas; ulcerative colitis; juvenile diabetes mellitus; proliferative glomerulonephritis; inflammatory bowel disease; multiple sclerosis; myasthenia gravis; rheumatoid and osteoarthritis; scleroderma; Chediak-Higashi and Sjogren's syndromes; systemic lupus erythematosus; thyroiditis; toxic shock syndrome; traumatic tissue damage; viral, bacterial, fungal and protozoal infections; and other physiologic/pathologic problems associated with induced, and otherwise abnormal, vesicular trafficking.

The nucleotide sequences encoding SNPG (or its complement) have numerous applications in techniques known to those skilled in the art of molecular biology. These techniques include use as hybridization probes, use as oligomers for PCR, use for chromosome and gene mapping, use in the recombinant production of SNPG, and use in generation of antisense DNA or RNA, their chemical analogs and the like. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

It will be appreciated by those skilled in the art that as a result of the degeneracy of the genetic code, a multitude of SNPG-encoding nucleotide sequences, some bearing minimal homology to the nucleotide sequences of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring SNPG, and all such variations are to be considered as being specifically disclosed.

Although nucleotide sequences which encode SNPG and its variants are preferably capable of hybridizing to the nucleotide sequence of the naturally occurring snpg under appropriately selected conditions of stringency, it may be advantageous to produce nucleotide sequences encoding SNPG or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding SNPG and its derivatives without altering the encoded amino acid sequences include the production of RNA transcripts having more desirable properties, such as a greater half-life, than transcripts produced from the naturally occurring sequence.

The nucleotide sequences encoding SNPG may be joined to a variety of other nucleotide sequences by means of well established recombinant DNA techniques (cf Sambrook J. et al. (1989) *Molecular Cloning: A Laboratory Manual,* Cold Spring Harbor Laboratory, Cold Spring Harbor N.Y.). Useful nucleotide sequences for joining to snpg include an assortment of cloning vectors, e.g., plasmids, cosmids, lambda phage derivatives, phagemids, and the like, that are well known in the art. Vectors of interest include expression vectors, replication vectors, probe generation vectors, and sequencing vectors. In general, vectors of interest will contain an origin of replication functional in at least one organism, convenient restriction endonuclease sensitive sites, and selectable markers for the host cell.

Another aspect of the subject invention is to provide for snpg specific nucleic acid hybridization probes capable of hybridizing with naturally occurring nucleotide sequences encoding SNPG. Such probes may also be used for the detection of related synaptogyrin encoding sequences and should preferably contain at least 50% of the nucleotides from any of these SNPG encoding sequences. The hybridization probes of the subject invention may be derived from the nucleotide sequence of the SEQ ID NOs:1 and 5–12 or from genomic sequence including promoter, enhancer elements and introns of the naturally occurring snpg. Hybridization probes may be labeled by a variety of reporter groups, including radionuclides such as $^{32}P$ or $^{35}S$, or enzymatic labels such as alkaline phosphatase coupled to the probe via avidin/biotin coupling systems, and the like.

PCR as described in U.S. Pat. Nos 4,683,195 and 4,965,188 provide additional uses for oligonucleotides based upon the nucleotide sequences which encode SNPG. Such probes used in PCR may be of recombinant origin, may be chemically synthesized, or a mixture of both. The probe will comprise a discrete nucleotide sequence for the detection of identical sequences or a degenerate pool of possible sequences for identification of closely related genomic sequences.

Other means for producing specific hybridization probes for snpg DNAs include the cloning of nucleic acid sequences encoding SNPG or SNPG derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

It is now possible to produce a DNA sequence, or portions thereof, encoding a SNPG and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a snpg sequence or any portion thereof.

The nucleotide sequences may be used to construct an assay to detect activation or induction of snpg due to inflammation or disease. The nucleotide sequence may be labeled by methods known in the art and added to a fluid or tissue sample from a patient under hybridizing conditions. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with the sample, and the assay indicates the presence of the inducing inflammation and/or disease.

The nucleotide sequences for snpg may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York N.Y.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of an snpg on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

The nucleotide sequence encoding SNPG may be used to produce purified SNPG using well known methods of recombinant DNA technology. Among the many publications that teach methods for the expression of genes after they have been isolated is Goeddel (1990) Gene Expression Technology, Methods and Enzymology, Vol 185, Academic Press, San Diego. SNPG may be expressed in a variety of host cells, either prokaryotic or eukaryotic. Host cells may be from the same species from which a particular snpg nucleotide sequence was isolated or from a different species. Advantages of producing SNPG by recombinant DNA technology include obtaining adequate amounts of the protein for purification and the availability of simplified purification procedures.

Cells transformed with DNA encoding SNPG may be cultured under conditions suitable for the expression of VAMPs and recovery of the protein. SNPG produced by a recombinant cell may be secreted, contained intracellularly, or inserted into a membrane depending on the particular genetic construction used. In general, it is more convenient to prepare recombinant proteins in secreted form. Purification steps vary with the production process, the host organism and the particular protein produced.

In addition to recombinant production, fragments of SNPG may be produced by direct peptide synthesis using solid-phase techniques (cf Stewart et al (1969) Solid-Phase Peptide Synthesis, W. H. Freeman Co, San Francisco; Merrifield J. (1963) J Am Chem Soc 85:2149–2154). In vitro protein synthesis may be performed using manual techniques or by automation. Automated synthesis may be achieved, for example, using Applied Biosystems 431A Peptide Synthesizer (ABI, Foster City, Calif.) in accordance with the instructions provided by the manufacturer. Various fragments of SNPG may be chemically synthesized separately and combined using chemical methods to produce the full length molecule.

SNPG for antibody induction does not require biological activity; however, the protein fragment, or oligopeptide must be immunogenic. Peptides used to induce specific antibodies may have an amino acid sequence consisting of at least five amino acids, preferably at least 10 amino acids. They should mimic a portion of the amino acid sequence of the natural protein and may contain the entire amino acid sequence of a small, naturally occurring molecule. Short stretches of SNPG amino acids may be fused with those of another protein such as keyhole limpet hemocyanin and antibody produced against the chimeric molecule.

Antibodies specific for SNPG may be produced by inoculation of an appropriate animal with the polypeptide or an antigenic fragment. An antibody is specific for the particular SNPG if it is produced against an epitope of the polypeptide and binds to at least part of the natural or recombinant protein. Antibody production includes not only the stimulation of an immune response by injection into animals, but also analogous steps in the production of synthetic antibodies or other specific-binding molecules such as the screening of recombinant immunoglobulin libraries (cf Orlandi R. et al (1989) PNAS 86:3833–3837, or Huse W. D. et al (1989) Science 256:1275–1281) or the in vitro stimulation of lymphocyte populations. Current technology (Winter G. and Milstein C. (1991) Nature 349:293–299) provides for a number of highly specific binding reagents based on the principles of antibody formation. These techniques may be adapted to produce molecules specifically binding SNPG.

An additional embodiment of the subject invention is the use of SNPG specific antibodies, as bioactive agents to treat conditions such as AIDS; allergies including hay fever, asthma, and urticaria (hives); autoimmune hemolytic anemia; cancers, leukemias or lymphomas; ulcerative colitis; juvenile diabetes mellitus; proliferative glomerulonephritis; inflammatory bowel disease; multiple sclerosis; myasthenia gravis; rheumatoid and osteoarthritis; scleroderma; Chediak-Higashi and Sjogren's syndromes; systemic lupus erythematosus; thyroiditis; toxic shock syndrome; traumatic tissue damage; viral, bacterial, fungal and protozoal infections; and other physiologic/pathologic problems associated with induced, and otherwise abnormal, vesicular trafficking.

Bioactive compositions comprising agonists or antagonists of SNPG may be administered in a suitable therapeutic dose determined by any of several methodologies including clinical studies on mammalian species to determine maximum tolerable dose and on normal human subjects to determine safe dosage. Additionally, the bioactive agent may be complexed with a variety of well established compounds or compositions which enhance stability or pharmacological properties such as half-life. It is contemplated that a therapeutic, bioactive composition may be delivered by intravenous infusion into the bloodstream or any other effective means which could be used for treatment.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to an oligopeptide, peptide, polypeptide or protein sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P. E. et al (1993) Anticancer Drug Des 8:53–63).

As used herein, SNPG refers to the amino acid sequence of SNPG from any species, particularly mammalian, including bovine, ovine, porcine, murine, equine, and preferably human, in a naturally occurring form or from any source whether natural, synthetic, semi-synthetic or recombinant. As used herein, "naturally occurring" refers to an amino acid sequence which is found in nature.

The present invention also encompasses SNPG variants. A preferred SNPG variant is one having at least 80% amino acid sequence similarity, a more preferred SNPG variant is one having at least 90% amino acid sequence similarity and a most preferred SNPG variant is one having at least 95% amino acid sequence similarity to the SNPG amino acid sequence (SEQ ID NO:2). A "variant" of SNPG may have an amino acid sequence that is different by one or more amino acid "substitutions". The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNASTAR software.

The term "biologically active" refers to an SNPG having structural, regulatory or biochemical functions of the naturally occurring SNPG. Likewise, "immunologically active" defines the capability of the natural, recombinant or synthetic SNPG, or any oligopeptide thereof, to induce a specific immune response in appropriate animals or cells and to bind with specific antibodies.

The term "derivative" as used herein refers to the chemical modification of an snpg or the encoded SNPG. Illustrative of such modifications would be replacement of hydrogen by an alkyl, acyl, or amino group. An SNPG derivative would encode a polypeptide which retains essential biological characteristics of natural SNPG.

As used herein, the term "purified" refers to molecules, either nucleic or amino acid sequences, that are removed from their natural environment and isolated or separated from at least one other component with which they are naturally associated.

The SNPG Coding Sequences

The nucleic acid and deduced amino acid sequences of SNPG are shown in FIGS. 1A and 1B. In accordance with the invention, any nucleic acid sequence which encodes the amino acid sequence of SNPG can be used to generate recombinant molecules which express SNPG. In a specific embodiment described herein, the sequence for snpg was first isolated as Incyte Clone 775426 from a colon cDNA library (COLNNOT05).

Methods for DNA sequencing are well known in the art and employ such enzymes as the Klenow fragment of DNA polymerase I, SEQUENASE® (U.S. Biochemical Corp, Cleveland Ohio, Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.).

Methods to extend the DNA from an oligonucleotide primer annealed to the DNA template of interest have been developed for both single-stranded and double-stranded templates. Chain termination reaction products were separated using electrophoresis and detected via their incorporated, labeled precursors. Recent improvements in mechanized reaction preparation, sequencing and analysis have permitted expansion in the number of sequences that can be determined per day. Preferably, the process is automated with machines such as the Hamilton Micro Lab 2200 (Hamilton, Reno Nev.), Peltier Thermal Cycler (PTC200; M. J. Research, Watertown Mass.) and the ABI 377 DNA sequencers (Perkin Elmer).

The quality of any particular cDNA library may be determined by performing a pilot scale analysis of the cDNAs and checking for percentages of clones containing vector, lambda or E. coli DNA, mitochondrial or repetitive DNA, and clones with exact or homologous matches to sequences in public databases.

Extending the Polynucleotide Sequence

The polynucleotide sequence of snpg may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T. et al (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M. et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Parker J. D. et al (1991; Nucleic Acids Res 19:3055–60), teach walking PCR, a method for targeted gene walking which permits retrieval of unknown sequence. PROMOTERFINDER™ a new kit available from Clontech (Palo Alto Calif.) uses PCR, nested primers and PROMOTERFINDER libraries to walk in genomic DNA. This process avoids the need to screen libraries and is useful in finding intron/exon junctions.

Another PCR method employs XL-PCR™ (Perkin Elmer) to amplify and extend nucleotide sequences.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

A new method for analyzing either the size or confirming the nucleotide sequence of sequencing or PCR products is capillary electrophoresis. Systems for rapid sequencing are available from Perkin Elmer, Beckman Instruments (Fullerton Calif.), and other companies. Capillary sequencing employs flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg. GENOTYPER™ and SEQUENCE NAVIGATOR™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M. C. et al (1993) Anal Chem 65:2851–8).

Expression of the Nucleotide Sequence

In accordance with the present invention, polynucleotide sequences which encode SNPG, fragments of the polypeptide, fusion proteins or functional equivalents thereof may be used to generate recombinant DNA molecules that direct the expression of SNPG in appropriate host cells. Due to the inherent degeneracy of the genetic code, other DNA sequences which encode substantially the same or a functionally equivalent amino acid sequence, may be used to clone and express SNPG. As will be understood by those of skill in the art, it may be advantageous to produce SNPG-encoding nucleotide sequences possessing non-naturally occurring codons. Codons preferred by a particular prokaryotic or eukaryotic host (Murray E. et al (1989) Nuc Acids Res 17:477–508) can be selected, for example, to increase the rate of SNPG expression or to produce recombinant RNA transcripts having desirable properties, such as a longer half-life, than transcripts produced from naturally occurring sequence.

Also included within the scope of the present invention are polynucleotide sequences that are capable of hybridizing to the nucleotide sequence of FIGS. 1A and 1B under various conditions of stringency. Hybridization conditions are based on the melting temperature (Tm) of the nucleic acid binding complex or probe, as taught in Berger and Kimmel (1987, *Guide to Molecular Cloning Techniques*, Methods in Enzymology, Vol 152, Academic Press, San Diego Calif.) incorporated herein by reference, and confer may be used at a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

The term "hybridization" as used herein shall include "any process by which a strand of nucleic acid joins with a complementary strand through base pairing" (Coombs J. (1994) *Dictionary of Biotechnology,* Stockton Press, New York N.Y.). Then by definition, hybridization includes the process of amplification as carried out in the polymerase chain reaction technologies described in Dieffenbach C. W. and G. S. Dveksler (1995, *PCR Primer, a Laboratory Manual,* Cold Spring Harbor Press, Plainview N.Y.) and incorporated herein by reference.

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring snpg.

A "substitution" results from the replacement of one or more nucleotides or amino acids by different nucleotides or amino acids, respectively.

Altered snpg nucleic acid sequences which may be used in accordance with the invention include deletions, insertions or substitutions of different nucleotides resulting in a polynucleotide that encodes the same or a functionally equivalent SNPG. The protein may also show deletions, insertions or substitutions of amino acid residues which produce a silent change and result in a functionally equivalent SNPG. Deliberate amino acid substitutions may be made on the basis of similarity in polarity, charge, solubility, hydrophobicity, hydrophilicity, and/or the amphipathic nature of the residues as long as the biological activity of SNPG is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of snpg. As used herein, an "allele" or "allelic sequence" is an alternative form of snpg. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

The nucleotide sequences of the present invention can be engineered in order to alter an snpg coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant snpg sequence may be ligated to a heterologous sequence to encode a fusion protein. For example, for screening of peptide libraries for inhibitors of SNPG activity, it may be useful to encode a chimeric SNPG protein that is recognized by a commercially available antibody. A fusion protein may also be engineered to contain a cleavage site located between an SNPG sequence and the heterologous protein sequence, so that the SNPG may be cleaved and purified away from the heterologous moiety.

In an alternate embodiment of the invention, the coding sequence of snpg could be synthesized, whole or in part, using chemical methods well known in the art (see Caruthers M. H. et al (1980) Nuc Acids Res Symp Ser 215–23, Horn T. et al(1980) Nuc Acids Res Symp Ser 225–32, etc). Alternatively, the protein itself could be produced using chemical methods to synthesize an SNPG amino acid sequence, whole or in part. For example, peptide synthesis can be performed using various solid-phase techniques (Roberge J. Y. et al (1995) Science 269:202–204) and automated synthesis may be achieved, for example, using the ABI 431A Peptide Synthesizer (Perkin Elmer) in accordance with the instructions provided by the manufacturer. The newly synthesized peptide can be purified by preparative high performance liquid chromatography (eg, Creighton (1983) *Proteins, Structures and Molecular Principles,* W. H. Freeman and Co, New York N.Y.). The composition of the synthetic peptides may be confirmed by amino acid analysis or sequencing (eg, the Edman degradation procedure; Creighton, supra). Additionally the amino acid sequence of SNPG, or any part thereof, may be altered during direct synthesis and/or combined using chemical methods with sequences from other proteins, or any part thereof, to produce a variant polypeptide.

Expression Systems

In order to express a biologically active SNPG, the nucleotide sequence encoding SNPG or its functional equivalent, is inserted into an appropriate expression vector, ie, a vector which contains the necessary elements for the transcription and translation of the inserted coding sequence.

Methods which are well known to those skilled in the art can be used to construct expression vectors containing an SNPG coding sequence and appropriate transcriptional or translational controls. These methods include in vitro recombinant DNA techniques, synthetic techniques and in vivo recombination or genetic recombination. Such techniques are described in Maniatis et al (1989) *Molecular Cloning, A Laboratory Manual,* Cold Spring Harbor Press, Plainview N.Y. and Ausubel F. M. et al. (1989) *Current Protocols in Molecular Biology,* John Wiley & Sons, New York N.Y.

A variety of expression vector/host systems may be utilized to contain and express an snpg coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the BLUE-SCRIPT® phagemid (Stratagene, LaJolla Calif.) or PSPORT1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of snpg, vectors based on SV40 or EBV may be used with an appropriate selectable marker.

In bacterial systems, a number of expression vectors may be selected depending upon the use intended for SNPG. For example, when large quantities of SNPG are needed for the induction of antibodies, vectors which direct high level expression of fusion proteins that are readily purified may be desirable. Such vectors include, but are not limited to, the multifunctional *E. coli* cloning and expression vectors such as BLUESCRIPT® (Stratagene), in which the snpg coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding SNPG may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J. and Sinibaldi R. M. (1991) Results Probl Cell Differ 17:85–105) may be used. These constructs can be introduced into plant cells by direct DNA transformation or pathogen-mediated transfection. For reviews of such techniques, see Hobbs S. or Murry L. E. in McGraw Yearbook of Science and Technology (1992) McGraw Hill New York N.Y., pp 191–196 or Weissbach and Weissbach (1988) Methods for Plant Molecular Biology, Academic Press, New York N.Y., pp 421–463.

An alternative expression system which could be used to express snpg is an insect system. In one such system, *Autographa californica* nuclear polyhedrosis virus (AcNPV) is used as a vector to express foreign genes in *Spodoptera frugiperda* cells or in *Trichoplusia larvae.* The snpg coding sequence may be cloned into a nonessential region of the virus, such as the polyhedrin gene, and placed under control of the polyhedrin promoter. Successful insertion of snpg will render the polyhedrin gene inactive and produce recombinant virus lacking coat protein coat. The recombinant viruses are then used to infect S. frugiperda cells or *Trichoplusia larvae* in which SNPG is expressed (Smith et al (1983) J Virol 46:584; Engelhard E. K. et al (1994) Proc Nat Acad Sci 91:3224–7).

In mammalian host cells, a number of viral-based expression systems may be utilized. In cases where an adenovirus is used as an expression vector, an snpg coding sequence may be ligated into an adenovirus transcription/translation complex consisting of the late promoter and tripartite leader sequence. Insertion in a nonessential E1 or E3 region of the viral genome will result in a viable virus capable of expressing SNPG in infected host cells. (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of an snpg sequence. These signals include the ATG initiation codon and adjacent sequences. In cases where snpg, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D. et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express snpg may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M. et al (1977) Cell 11:223–32) and adenine phosphoribosyltransferase (Lowy I. et al (1980) Cell 22:817–23) genes which can be employed in tk_ or aprt_ cells, respectively. Also, antimetabolite, antibiotic or herbicide resistance can be used as the basis for selection; for example, dhfr which confers resistance to methotrexate (Wigler M. et al (1980) Proc Natl Acad Sci 77:3567–70); npt, which confers resistance to the aminoglycosides neomycin and G-418 (Colbere-Garapin F. et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S. C. and R. C. Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C. A. et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the snpg is inserted within a marker gene sequence, recombinant cells containing snpg can be identified by the absence of marker gene function. Alternatively, a marker gene can be placed in tandem with an SNPG sequence under the control of a single promoter. Expression of the marker gene in response to induction or selection usually indicates expression of the tandem snpg as well.

Alternatively, host cells which contain the coding sequence for snpg and express SNPG may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the snpg polynucleotide sequence can be detected by DNA-DNA or DNA-RNA hybridization or amplification using probes, portions or fragments of snpg. Nucleic acid amplification based assays involve the use of oligonucleotides or oligomers based on the snpg sequence to detect transformants containing snpg DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of SNPG, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on SNPG is preferred, but a competitive binding assay may be employed. These and other assays are described, among other places, in Hampton R. et al (1990, *Serological Methods, a Laboratory Manual,* APS Press, St Paul Minn.) and Maddox D. E. et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to snpg include oligolabeling, nick translation, end-labeling or PCR amplification using a labeled nucleotide. Alternatively, the snpg sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and U.S. Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277, 437; 4,275,149 and 4,366,241. Also, recombinant immunoglobulins may be produced as shown in U.S. Pat. No. 4,816,567 incorporated herein by reference.

Purification of SNPG

Host cells transformed with an SNPG nucleotide sequence may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing snpg can be designed with signal sequences which direct secretion of SNPG through a prokaryotic or eukaryotic cell membrane. Other recombinant constructions may join snpg to nucleotide sequence encoding a polypeptide domain which will facilitate purification of soluble proteins (Kroll D. J. et al (1993) DNA Cell Biol 12:441–53; of discussion of vectors infra containing fusion proteins).

SNPG may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and SNPG is useful to facilitate purification.

Uses of SNPG

Figure 3A:
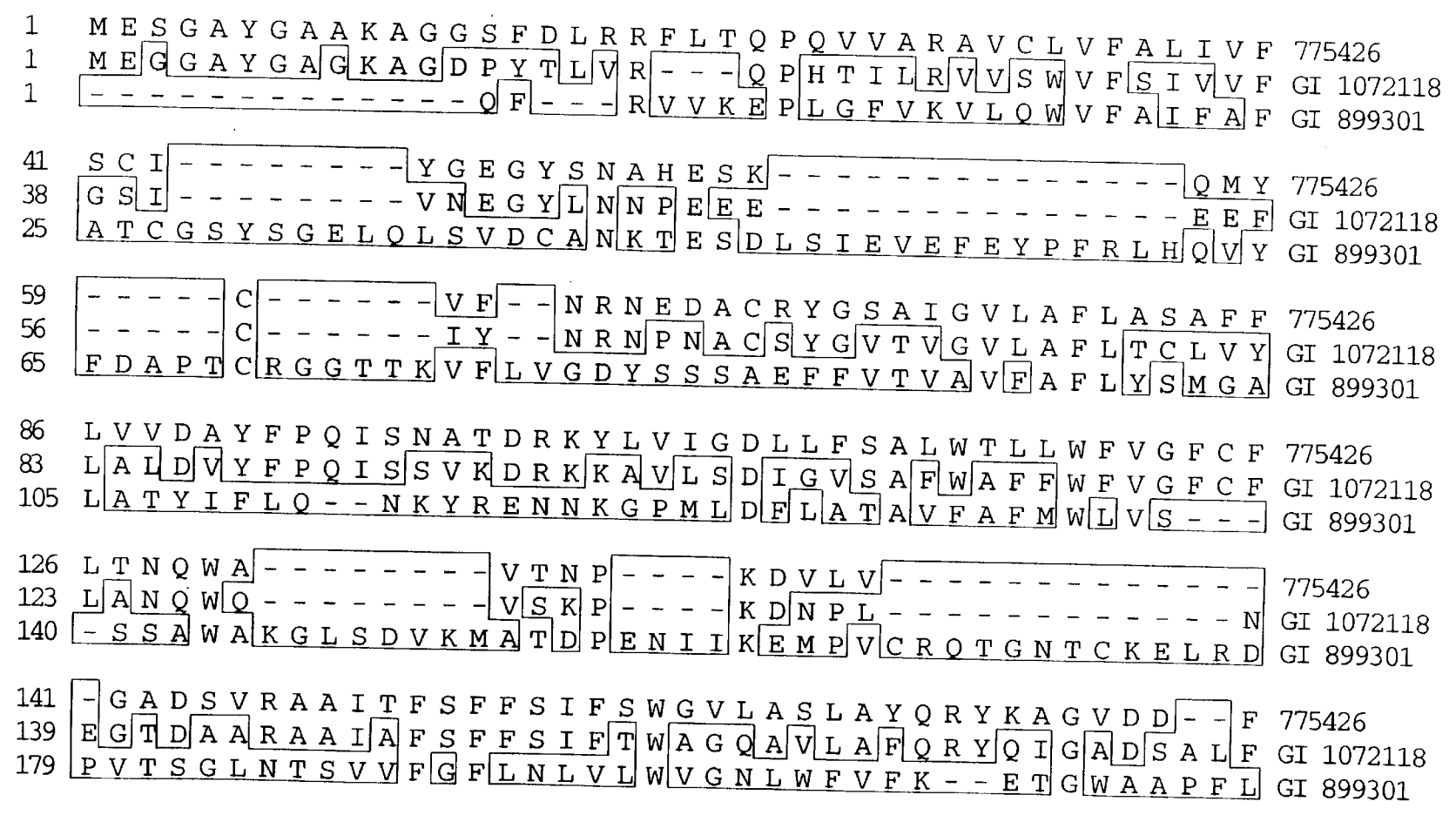
Figure 3B:
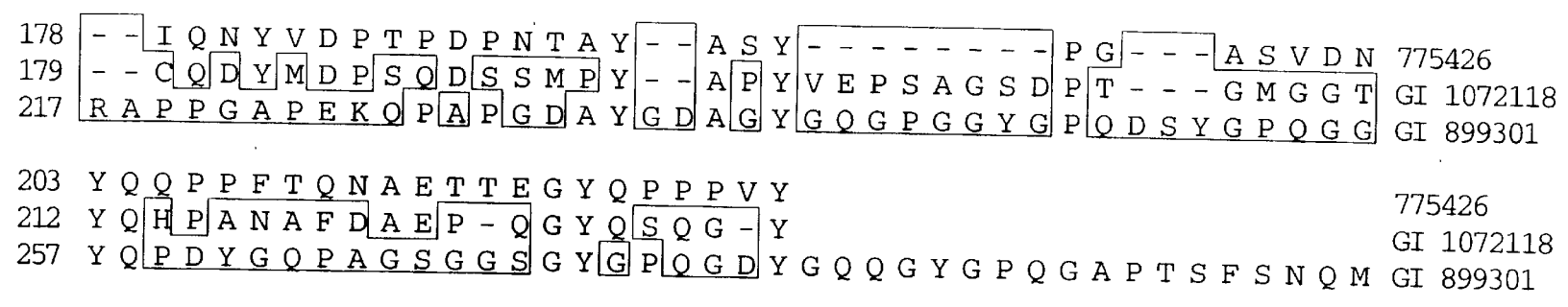

The rationale for diagnostic and therapeutic uses of SNPG sequences is based on the disclosed nucleic acid and amino acid sequences, the homology between SNPG, rat synaptogyrin FIGS. 3A and 3B, and the presence of the snpg transcript in the eight cDNA libraries made from the tissues of patients with specific disease states or subjects who died traumatically.

The nucleic acid sequence (SEQ ID NO:1), its complement, fragments or oligomers, and anti-SNPG antibodies may be used as diagnostic compositions to assay bodily fluids or extracts of biological samples for expression of snpg. Purified polynucleotides and polypeptides can be used as positive controls in their respective nucleic acid or protein based assays to validate and quantitate the expression of snpg either during preliminary diagnosis or during the course of therapeutic treatment for a particular condition or disease. In some cases, the mere presence of snpg or SNPG (expression vs. absence of expression) will connote disease, while in other cases, snpg expression will be abnormal because snpg or SNPG deviates from a predetermined normal level.

The nucleic acid sequence, its complement, fragments or oligomers, and anti-SNPG antibodies are useful in diagnostic assays for evaluating disease-associated expression of snpg. Some of the diseases in which snpg expression may be implicated include AIDS; allergies including hay fever, asthma, and urticaria (hives); autoimmune hemolytic anemia; cancers, leukemias or lymphomas; ulcerative colitis; juvenile diabetes mellitus; proliferative glomerulonephritis; inflammatory bowel disease; multiple sclerosis; myasthenia gravis; rheumatoid and osteoarthritis; scleroderma; Chediak-Higashi and Sjogren's syndromes; systemic lupus erythematosus; thyroiditis; toxic shock syndrome; traumatic tissue damage; viral, bacterial, fungal and protozoal infections; and other physiologic/pathologic problems associated with induced, and otherwise abnormal, vesicular trafficking. For example, the expression of snpg in the colon tissue removed from the 40 year old male with Crohn's disease suggests that the naturally occurring protein was being expressed and secreted in association with Crohn's disease.

Antisense molecules, PNAs, antibodies, antagonists or inhibitors can all be used as pharmaceutical compositions. Delivery of these molecules for therapeutic purposes in any of the disease states listed above is further described under Pharmaceutical Compositions. The most appropriate therapy depends on the patient, the specific diagnosis, and the physician who is treating and monitoring the patient's condition.

The SNPG disclosed herein can be used to direct vesicular localization. Artificial vesicles containing SNPG can be designed to carry therapeutic chemical or biological molecules to a particular target. Once the number, arrangement and specificity of SNPG in both intracellular and extracellular trafficking is obtained, use of the protein offers not only the ability to target therapeutics but the ability to disrupt vesicular processes; specific intervention in particular disease states.

The artificial vesicles most resemble liposomes and may be sterically stabilized. The SNPG acts as an address to direct the movement of the vesicle into, through or out of the cell. Both the number and distribution of the SNPG and the contents of the vesicles are carefully selected. This technology is also potentially useful for the delivery of vectors and recombinant nucleotides to effect a localized, heritable or nonheritable cell therapy. Specifically, the artificial vesicle is addressed to a particular cell type, tissue, organ or tumor by the SNPG.

Another use for the SNPG involves modification of an intravesicular loop of SNPG. In this case, the SNPG is chimeric and the loop between appropriate cysteine residues consists of a therapeutic peptide. The therapeutic peptide is protected within the vesicle during delivery; and at the time of membrane fusion is exposed. The exposed peptide either carries out its function while still anchored to the membrane or is cleaved at a predetermined sequence by a constitutive intracellular enzyme and released. A preferred embodiment of the invention includes the delivery of short therapeutic peptides in this manner.

SNPG Antibodies

Procedures well known in the art can be used for the production of antibodies to SNPG Such antibodies include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

For the production of antibodies, various hosts including goats, rabbits, rats, mice, etc may be immunized by injection with SNPG or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to SNPG may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R. Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S.

Pat. No. 4,946,778) can be adapted to produce SNPG-specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G. and Milstein C. (1991; Nature 349:293–299).

Antibody fragments which contain specific binding sites for SNPG may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse W. D. et al (1989) Science 256:1275–1281).

SNPG-specific antibodies are useful for the diagnosis of conditions and diseases associated with expression of SNPG. A variety of protocols for competitive binding or immunoradiometric assays using either polyclonal or monoclonal antibodies with established specificities are well known in the art. Such immunoassays typically involve the formation of complexes between SNPG and its specific antibody and the measurement of complex formation. A two-site, monoclonal-based immunoassay utilizing monoclonal antibodies reactive to two noninterfering epitopes on a specific SNPG protein is preferred, but a competitive binding assay may also be employed. These assays are described in Maddox D. E. et al (1983, J Exp Med 158:1211).

Diagnostic Assays Using SNPG Specific Antibodies

Particular SNPG antibodies are useful for the diagnosis of conditions or diseases characterized by expression of SNPG or in assays to monitor patients being treated with antagonists or inhibitors of SNPG. Diagnostic assays for SNPG include methods utilizing the antibody and a label to detect SNPG in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring SNPG, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on SNPG is preferred, but a competitive binding assay may be employed. These assays are described, among other places, in Maddox, D. E. et al (1983, J Exp Med 158:1211).

In order to provide a basis for diagnosis, normal or standard values for SNPG expression must be established. This is accomplished by combining body fluids or cell extracts taken from normal subjects, either animal or human, with antibody to SNPG under conditions suitable for complex formation which are well known in the art. The amount of standard complex formation may be quantified by comparing various artificial membranes containing known quantities of SNPG with both control and disease samples from biopsied tissues. Then, standard values obtained from normal samples may be compared with values obtained from samples from subjects potentially affected by disease. Deviation between standard and subject values establishes the presence of disease state.

Drug Screening

SNPG, its catalytic or immunogenic fragments or oligopeptides, can be used for screening therapeutic compounds in any of a variety of drug screening techniques. The fragment employed in such a test may be free in solution, affixed to a solid support, borne on a cell surface, or located intracellularly. The formation of binding complexes, between SNPG and the agent being tested, may be measured.

Another technique for drug screening which provides for high throughput screening of compounds having suitable binding affinity to the SNPG is described in detail in "Determination of Amino Acid Sequence Antigenicity" by Geysen H. N., WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of SNPG and washed. Bound SNPG is then detected by methods well known in the art. Purified SNPG can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding SNPG specifically compete with a test compound for binding SNPG. In this manner, the antibodies can be used to detect the presence of any peptide which shares one or more antigenic determinants with SNPG.

Uses of the Polynucleotide Encoding SNPG

A polynucleotide, snpg, or any part thereof, may be used for diagnostic and/or therapeutic purposes. For diagnostic purposes, the snpg of this invention may be used to detect and quantitate gene expression in biopsied tissues in which expression of SNPG may be implicated. The diagnostic assay is useful to distinguish between absence, presence, and excess expression of snpg and to monitor regulation of snpg levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding SNPG or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring snpg, alleles or related sequences.

Diagnostics

Polynucleotide sequences encoding SNPG may be used for the diagnosis of conditions or diseases with which the expression of SNPG is associated. For example, polynucleotide sequences encoding SNPG may be used in hybridization or PCR assays of fluids or tissues from biopsies to detect snpg expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

Such assays may be also be used to evaluate the efficacy of a particular therapeutic treatment regime in animal studies, in clinical trials, or in monitoring the treatment of an individual patient. In order to provide a basis for the diagnosis of disease, a normal or standard profile for snpg expression must be established. This is accomplished by combining body fluids or cell extracts taken from normal subjects, either animal or human, with snpg, or a portion thereof, under conditions suitable for hybridization or amplification. Standard hybridization may be quantified by comparing the values obtained for normal subjects with a dilution series of snpg run in the same experiment where a known amount of purified snpg is used. Standard values obtained from normal samples may be compared with values obtained from samples from patients affected by snpg-associated diseases. Deviation between standard and subject values establishes the presence of disease.

Once disease is established, a therapeutic agent is administered; and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR as described in U.S. Pat. Nos. 4,683,195 and 4,965,188 provides additional uses for oligonucleotides based upon the snpg sequence. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods to quantitate the expression of a particular molecule include radiolabeling (Melby P. C. et al 1993 J Immunol Methods 159:235–44) or biotinylating (Duplaa C. et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. For example, the presence of snpg in extracts of biopsied tissues may indicate the onset of cancer. A definitive diagnosis of this type may allow health professionals to begin aggressive treatment and prevent further worsening of the condition. Similarly, further assays can be used to monitor the progress of a patient during treatment.

Therapeutic

The polynucleotide disclosed herein may be useful in the treatment of various inherited conditions or diseases such as Crohn's disease, rheumatoid arthritis, asthma, and cancers or tumors of the colon, lung and brain. By introducing the antisense molecules (anti-snpg) into the lungs, gene therapy can be used to reduce or eliminate SNPG expression. In such instances, flooding the cell with an antisense molecule prevents translation of the amino acid sequence.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express anti-snpg. See, for example, the techniques described in Maniatis et al (supra) and Ausubel et al (supra).

The polynucleotides comprising full length cDNA sequence and/or its regulatory elements enable researchers to use snpg as an investigative tool in sense (Youssoufian H. and H. F. Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding SNPG can be turned off by transfecting a cell or tissue with expression vectors which express high levels of the desired fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of snpg, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J. E. et al. (In: Huber B. E. and B. I. Carr (1994) *Molecular and Immunologic Approaches,* Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of snpg.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding SNPG. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient as presented in U.S. Pat. Nos. 5 5,399,493 and 5,437,994, disclosed herein by reference. Delivery by transfection and by liposome are quite well known in the art.

Furthermore, the nucleotide sequences for snpg disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for snpg can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C. M. (1993; Blood Rev 7:127–34) and Trask B. J. (1991; Trends Genet 7:149–54).

In situ hybridization of chromosomal preparations and physical mapping techniques such as linkage analysis using established chromosomal markers are invaluable in extending genetic maps. A recent example of an STS based map of the human genome was recently published by the Whitehead-MIT Center for Genomic Research (Hudson T. J. et al. (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention comprises pharmaceutical compositions which may comprise nucleotides, proteins, antibodies, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 histidine, 0.1%–2% sucrose, 2%–7% mannitol at a pH range of 4.5 to 5.5 that is combined with buffer prior to use.

After pharmaceutical compositions comprising a compound of the invention formulated in an acceptable carrier have been prepared, they can be placed in an appropriate container and labeled for treatment of an indicated condition. For administration of SNPG, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

It is contemplated an antisense molecules or anti-SNPG antibody can be delivered in a suitable formulation to block the expression of snpg or the vesicle address system governed by SNPG in the lung of asthmatics. In a clinical setting, the monitoring of respiration allows the attending physician to adjust dosage of the antisense molecule or antibody in a range which restores normal lung function. Similarly, administration of antagonists or inhibitors of SNPG and monitoring of the patient's condition should minimize undesired side effects.

The examples below are provided to illustrate the subject invention and are not included for the purpose of limiting the invention.

EXAMPLES

I Colon cDNA Library Construction

Incyte Clone 775426 was identified among the partial cDNAs isolated from a colon cDNA library (COLNNOT05). The COLNNOT05 library was constructed from normal appearing sigmoid colon tissue obtained from a 40 year old Caucasian male with Crohn's Disease in the ascending colon who had undergone a partial colorectomy and anal fistulotomy. A permanent ileostomy was also established. There were additional diagnoses of functional diarrhea, oral candidiasis, a perianal abscess and a secondary malignant colorectal neoplasm. The patient history indicated type I diabetes mellitus which was being treated with insulin and benign hypertension for which medication was not prescribed. Also reported in the patient history was an episode of unspecified viral meningitis, anorexia, pulmonary insufficiency associated with continuous tobacco use, and repair of an inguinal hernia. At the time of surgery the patient was taking Zantac (ranitidine hydrochloride; Glaxo Pharmaceuticals, Research Park Triangle North Caroline) to inhibit gastric acid secretion. Prednisone therapy and Anusol (hydrocortisone; Parke Davis, Morris Plains N.J.) were also prescribed for treatment of his gastrointestinal disease.

The frozen tissue was homogenized using a Brinkmann Homogenizer Polytron PT-3000 (Brinkmann Instruments, Westbury N.J.) and lysed immediately in a buffer containing guanidinium isothiocyanate. The lysate was then loaded on a 5.7M CsCl cushion and ultracentrifuged in an SW28 swinging bucket rotor on a Beckman L8-70M Ultracentrifuge (Beckman Instruments) for 18 hours at 25,000 rpm at ambient temperature. RNA was extracted using a Qiagen Total RNA Maxi Kit (QIAGEN Inc, Chatsworth Calif.), following the protocol without modification. The recovered RNA pellet was resuspended in DEPC treated water and DNase treated at 37° C. The RNA was then re-extracted with acid phenol pH 4.0, reprecipitated with 0.3M sodium acetate and 2.5 volume ethanol, and isolated using the QIAGEN OLIGOTEX kit (Qiagen). Approximately 1.4 micrograms of isolated polyA RNA was handled according to the recommended protocols in the SuperScript Plasmid System for cDNA Synthesis and Plasmid Cloning (catalog #18248-013; Gibco/BRL, Gaithersburg Md.). The cDNAs were fractionated on a Sepharose CL4B column (catalog #275105, Pharmacia), and those cDNAs exceeding 400 bp were ligated into PSPORT 1. The plasmid PSPORT 1 was subsequently transformed into DH5α competent cells (Cat. #18258-012, Gibco/BRL).

II Isolation and Sequencing of cDNA Clones

Plasmid DNA was released from the cells and purified using the Miniprep Kit (Catalog #77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Catalog #22711, Gibco/BRL) with carbenicillin at 25 mg/L and glycerol at 0.4%; 2) the bacteria were cultured for 24 hours after the wells were inoculated and then lysed; 3) the lysate was centrifuged using a Beckman GR rotor at 2900 rpm for 5 minutes before the contents of the block were added to the primary filter plate; and 4) the optional step of adding isopropanol to TRIS buffer was not routinely performed. After the last step in the protocol, samples were transferred to a Beckman 96 well block for storage.

The cDNAs were sequenced by the method of Sanger F. and A. R. Coulson (1975; J Mol Biol 94:441f), using a Hamilton Micro Lab 2200 (Hamilton, Reno Nev.) in combination with four Peltier Thermal Cyclers (PTC200 from M. J. Research, Watertown Mass.) and Applied Biosystems 377 or 373 DNA Sequencing Systems; and the reading frame was determined.

III Homology Searching of cDNA Clones and Their Deduced Proteins

Each cDNA was compared to sequences in GenBank using a search algorithm developed by Applied Biosystems and incorporated into the INHERIT™ 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S. F. (1993) J Mol Evol 36:290–300; Altschul, S. F. et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Extension of SNPG to Full Length or to Recover Regulatory Elements

The nucleic acid sequence of full length SNPG (SEQ ID NO:1) may be used to design oligonucleotide primers for extending a partial nculeotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known SNPG sequence "outward" generating amplicons containing new, unknown nucleotide sequence for the region of interest. The initial primers may be designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original cDNA library may be used to extend the sequence or a human genomic library is used to extend and amplify 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M. J. Research, Watertown Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 40° C. (and holding)

A 5–10 µl aliquot of the reaction mixture is analyzed by electrophoresis on a low concentration (about 0.6–0.8%) agarose mini-gel to determine which reactions were successful in extending the sequence. The largest products or bands were selected and cut out of the gel. Further purification involves using a commercial gel extraction method such as QIAQUICK® (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook J. et al, supra). After incubation for one hour at 37° C., the whole transformation mixture is plated on Luria Bertani (LB)-agar (Sambrook J. et al, supra) containing 2×Carb. The following day, several colonies are randomly picked from each plate and cultured in 150 µl of liquid LB/2×Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well. Amplification is performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 40° C. (and holding)

Aliquots of the PCR reactions are run on agarose gels together with molecular weight markers. The sizes of the PCR products are compared to the original partial cDNAs, and appropriate clones are selected, ligated into plasmid and sequenced.

V Labeling of Hybridization Probes

Hybridization probes derived from SEQ ID NO:1 may be employed to screen cDNAs, genomic DNAs or mRNAs. Although the labeling of oligonucleotides, consisting of about 20 base-pairs, is specifically described, essentially the same procedure may be used with larger cDNA fragments. Oligonucleotides are designed using state-of-the-art software such as OLIGO 4.06 (National Biosciences), labeled by combining 50 pmol of each oligomer and 250 mCi of [$\gamma$-$^{32}$P] adenosine triphosphate (Amersham, Chicago Ill.) and T4 polynucleotide kinase (DuPont NEN®, Boston Mass.). The labeled oligonucleotides are purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR® film (Kodak, Rochester N.Y.) is exposed to the blots in a Phosphoimager cassette (Molecular Dynamics, Sunnyvale Calif.) for several hours, hybridization patterns are compared visually.

VI Antisense Molecules

The snpg sequence, or any part thereof, may be used to inhibit in vivo or in vitro expression of native snpg. Although use of antisense oligonucleotides, comprising about 20 base-pairs, is specifically described, essentially the same procedure may be used with larger cDNA fragments. An oligonucleotide based on the coding sequence of SNPG as shown in FIGS. 1A and 1B may be used to inhibit expression of native SNPG. The complementary oligonucleotide can be designed from the most unique 5' sequence as shown in FIGS. 2A, 2B, 2C, 2D, 2E, 2F, 2G, 2H and 2I and used either to inhibit transcription by preventing promoter binding to the upstream nontranslated sequence or translation of an snpg transcript by preventing the ribosome from binding. Using an appropriate portion of the leader and 5' sequence of SEQ ID NO:1, an effective antisense oligonucleotide would include approximately 66 codons spanning the region which translates into the first 22 residues of the signal and coding sequence of the polypeptide as shown in FIGS. 1A and 1B.

VII Expression of SNPG

Expression of the SNPG may be accomplished by subcloning the cDNAs into appropriate vectors and transfecting the vectors into host cells. In this case, the cloning vector, PSPORT, previously used for the generation of the cDNA library is used to express SNPG in E. coli. Upstream of the cloning site, this vector contains a promoter for $\beta$-galactosidase, followed by sequence containing the amino-terminal Met and the subsequent 7 residues of $\beta$-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of $\beta$-galactosidase, about 5 to 15 residues of linker, and the full length SNPG. The signal sequence directs the secretion of SNPG into the bacterial growth media which can be used directly in the following assay for activity.

VIII SNPG Activity

A construct containing snpg is transformed into CHO cell and the expression of the construct is induced. The vesicular localization of SNPG is examined using microscopy and a fluorescent antibody specific for extra-membrane portions of SNPG. The number, arrangement, specificity and pathway of vesicles containing SNPG is examined. The search includes various cellular components such as ER, Golgi bodies, peroxisomes, lysosomes, and the plasmalemma and produces the information important to disrupt vesicular processes in disease intervention (asthma, tumors, etc.) and to allow for the development of sterically stabilized artificial vesicles which can deliver therapeutic chemical and biological molecules to effect a localized, heritable or nonheritable cell therapy.

IX Production of SNPG Specific Antibodies

Although SNPG purified using PAGE electrophoresis (Maniatis, supra) can be used to immunize rabbits using standard protocols, a monoclonal approach is more commonly employed. The amino acid sequence translated from SNPG is analyzed using DNASTAR software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions is described by Ausubel F. M. et al (supra) and shown in FIG. 4.

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel F. M. et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

X Purification of Native SNPG Using Specific Antibodies

Native or recombinant SNPG can be purified by immunoaffinity chromatography using antibodies specific for SNPG. An immunoaffinity column is constructed by covalently coupling SNPG antibody to an activated chromatographic resin such as CnBr-activated Sepharose (Pharmacia Biotech). After the coupling, the resin is blocked and washed according to the manufacturer's instructions.

Media containing SNPG is passed over the immunoaffinity column, and the column is washed under conditions that allow the preferential absorbance of SNPG (eg, high ionic strength buffers in the presence of detergent). The column is eluted under conditions that disrupt antibody/SNPG binding (eg, a buffer of pH 2–3 or a high concentration of a chaotrope such as urea or thiocyanate ion), and SNPG is collected.

XI Identification of Molecules Which Interact with SNPG

SNPG, or biologically active fragments thereof, are labelled with $^{125}$I Bolton-Hunter reagent (Bolton, A. E. and Hunter, W. M. (1973) Biochem J 133: 529). Candidate molecules previously arrayed in the wells of a 96 well plate are incubated with the labelled SNPG, washed and any wells with labelled SNPG complex are assayed. Data obtained using different concentrations of SNPG are used to calculate values for the number, affinity, and association of SNPG with the candidate molecules.

XII Artificial Vesicles for Delivery of Therapeutic Molecules

The vesicular localization directed by a particular SNPG and the intracellular and extracellular receptors with which SNPG interacts are examined using fluorescent antibody. The number, arrangement and specificity of SNPG are examined for vesicles involved in both intracellular and extracellular trafficking. The number and arrangement of SNPG molecules acts as an address label to target the vesicle through or out of the cell. Both the address and the contents of the vesicles are carefully selected. The artificial vesicles will have a particular size and the potential to deliver a chemical effector, a nucleotide such as an antisense sequence or a chemotherapeutic molecule such as DNase or a proteinase. This technology is also potentially useful for the delivery of vectors and recombinant nucleotides to effect a localized, heritable or nonheritable cell therapy.

XIII Chimeric, Therapeutic SNPG

In another embodiment, the intravesicular end of the SNPG molecule on an artificial vesicle is chimeric and consists of a therapeutic peptide. The therapeutic peptide is protected within the vesicle during delivery; and at the time of fusion, it is exposed. The exposed peptide either carries out its function while still anchored to the membrane or is cleaved at a predetermined sequence by a constitutive intracellular enzyme and released into the interior of the cell compartment or intercellular space. A preferred embodiment of the invention includes the delivery of short therapeutic peptides in this manner.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A purified polynucleotide encoding a polypeptide with an amino acid sequence shown in SEQ ID NO:2.

2. The polynucleotide of claim 1 having the nucleic acid sequence consisting of SEQ ID NO:1, or its complement.

3. A method for detecting the polynucleotide of claim 1 in a biological sample, the method comprising the steps of:
   a) combining the biological sample with the polynucleotide of claim 1, under conditions suitable for the formation of hybridization complex; and
   b) detecting the hybridization complex.

4. An expression vector comprising the polynucleotide of claim 2.

5. A host cell transformed with the expression vector of claim 4.

6. A method for producing a polypeptide having the amino acid sequence consisting of SEQ ID NO:2, the method comprising the steps of:
   a) culturing the host cell of claim 5 under conditions suitable for the expression of the polypeptide; and
   b) recovering the polypeptide from the host cell culture.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 969 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: COLNNOT05

(B) CLONE: 775426

(x i) SEQUENCE DESCRIPTION: SEQ ID NO:1:

| | | | | | |
|---|---|---|---|---|---|
| CAGTCGTGTA | ATACGACTCA | CTATAGGGAA | AGCTGGTTAC | GCCTGCAGGT | ACCGGTCCGG   60 |
| AATTCCCGGG | TCGACCCACG | CGTCCGGCGG | CAGCGGCGGC | GACGGCGACA | TGGAGAGCGG  120 |
| GGCCTACGGC | GCGGCCAAGG | CGGGCGGCTC | CTTCGACCTG | CGGCGCTTCC | TGACGCAGCC  180 |
| GCAGGTGGTG | GCGCGCGCCG | TGTGCTTGGT | CTTCGCCTTG | ATCGTGTTCT | CCTGCATCTA  240 |
| TGGTGAGGGC | TACAGCAATG | CCCACGAGTC | TAAGCAGATG | TACTGCGTGT | TCAACCGCAA  300 |
| CGAGGATGCC | TGCCGCTATG | GCAGTGCCAT | CGGGGTGCTG | GCCTTCCTGG | CCTCGGCCTT  360 |
| CTTCTTGGTG | GTCGACGCGT | ATTTCCCCCA | GATCAGCAAC | GCCACTGACC | GCAAGTACCT  420 |
| GGTCATTGGT | GACCTGCTCT | TCTCAGCTCT | CTGGACCTTG | CTGTGGTTTG | TTGGTTTCTG  480 |
| CTTCCTCACC | AACCAGTGGG | CAGTCACCAA | CCCGAAGGAC | GTGCTGGTGG | GGGCCGACTC  540 |
| TGTGAGGGCA | GCCATCACCT | TCAGCTTCTT | TTCCATCTTC | TCCTGGGGTG | TGCTGGCCTC  600 |
| CCTGGCCTAC | CAGCGCTACA | AGGCTGGCGT | GGACGACTTC | ATCCAGAATT | ACGTTGACCC  660 |
| CACTCCGGAC | CCCAACACTG | CCTACGCCTC | CTACCCAGGT | GCATCTGTGG | ACAACTACCA  720 |
| ACAGCCACCC | TTCACCCAGA | ACGCGGAGAC | CACCGAGGGC | TACCAGCCGC | CCCTGTGTA  780 |
| CTGAGCGGCG | GTTAGCGTGG | GAAGGGGGAC | AGAGAGGGCC | CTCCCCTCTG | CCCTGGACTT  840 |
| TCCCATGAGC | CTCCTGGAAC | TGCCAGCCCC | TCTCTTTCAC | CTGTTCCATC | CTGTGCAGCT  900 |
| GACACACAGC | TAAGGAGCCT | CATAGCCTGG | CGGGGGCTGG | CAGAGCCACA | CCCCAAGTGC  960 |
| CTGTGCCCA | | | | |  969 |

(2) INFORMATION FOR SEQ ID NO:2:

(i) SEQUENCE CHARACTERISTICS:
        (A) LENGTH: 224 amino acids
        (B) TYPE: amino acid
        (C) STRANDEDNESS: single
        (D) TOPOLOGY: linear (i i) MOLECULE TYPE: peptide (v i i) IMMEDIATE SOURCE:
        (A) LIBRARY: COLNNOT05
        (B) CLONE: 775426

(x i) SEQUENCE DESCRIPTION: SEQ ID NO:2:

| Met | Glu | Ser | Gly | Ala | Tyr | Gly | Ala | Ala | Lys | Ala | Gly | Gly | Ser | Phe | Asp |
|---|---|---|---|---|---|---|---|---|---|---|---|---|---|---|---|
| 1 | | | | 5 | | | | | 10 | | | | | 15 | |

| Leu | Arg | Arg | Phe | Leu | Thr | Gln | Pro | Gln | Val | Val | Ala | Arg | Ala | Val | Cys |
|---|---|---|---|---|---|---|---|---|---|---|---|---|---|---|---|
| | | | | 20 | | | | 25 | | | | | 30 | | |

| Leu | Val | Phe | Ala | Leu | Ile | Val | Phe | Ser | Cys | Ile | Tyr | Gly | Glu | Gly | Tyr |
|---|---|---|---|---|---|---|---|---|---|---|---|---|---|---|---|
| | | | 35 | | | | 40 | | | | | 45 | | | |

| Ser | Asn | Ala | His | Glu | Ser | Lys | Gln | Met | Tyr | Cys | Val | Phe | Asn | Arg | Asn |
|---|---|---|---|---|---|---|---|---|---|---|---|---|---|---|---|
| | 50 | | | | | 55 | | | | | 60 | | | | |

| Glu | Asp | Ala | Cys | Arg | Tyr | Gly | Ser | Ala | Ile | Gly | Val | Leu | Ala | Phe | Leu |
|---|---|---|---|---|---|---|---|---|---|---|---|---|---|---|---|
| 65 | | | | | 70 | | | | | 75 | | | | | 80 |

| Ala | Ser | Ala | Phe | Phe | Leu | Val | Val | Asp | Ala | Tyr | Phe | Pro | Gln | Ile | Ser |
|---|---|---|---|---|---|---|---|---|---|---|---|---|---|---|---|
| | | | | 85 | | | | | 90 | | | | | 95 | |

| Asn | Ala | Thr | Asp | Arg | Lys | Tyr | Leu | Val | Ile | Gly | Asp | Leu | Leu | Phe | Ser |
|---|---|---|---|---|---|---|---|---|---|---|---|---|---|---|---|
| | | | 100 | | | | | 105 | | | | | 110 | | |

| Ala | Leu | Trp | Thr | Leu | Leu | Trp | Phe | Val | Gly | Phe | Cys | Phe | Leu | Thr | Asn |
|---|---|---|---|---|---|---|---|---|---|---|---|---|---|---|---|
| | | 115 | | | | | 120 | | | | | 125 | | | |

| Gln | Trp | Ala | Val | Thr | Asn | Pro | Lys | Asp | Val | Leu | Val | Gly | Ala | Asp | Ser |
|---|---|---|---|---|---|---|---|---|---|---|---|---|---|---|---|

```
                    130                      135                    140
Val  Arg  Ala  Ala  Ile  Thr  Phe  Ser  Phe  Phe  Ser  Ile  Phe  Ser  Trp  Gly
145                      150                      155                     160

Val  Leu  Ala  Ser  Leu  Ala  Tyr  Gln  Arg  Tyr  Lys  Ala  Gly  Val  Asp  Asp
                    165                      170                     175

Phe  Ile  Gln  Asn  Tyr  Val  Asp  Pro  Thr  Pro  Asp  Pro  Asn  Thr  Ala  Tyr
               180                      185                     190

Ala  Ser  Tyr  Pro  Gly  Ala  Ser  Val  Asp  Asn  Tyr  Gln  Gln  Pro  Pro  Phe
          195                      200                     205

Thr  Gln  Asn  Ala  Glu  Thr  Thr  Glu  Gly  Tyr  Gln  Pro  Pro  Pro  Val  Tyr
     210                      215                     220
```

( 2 ) INFORMATION FOR SEQ ID NO:3:

( i ) SEQUENCE CHARACTERISTICS:
      ( A ) LENGTH: 231 amino acids
      ( B ) TYPE: amino acid
      ( C ) STRANDEDNESS: single
      ( D ) TOPOLOGY: linear ( i i ) MOLECULE TYPE: peptide ( v i i ) IMMEDIATE SOURCE:
      ( A ) LIBRARY: GenBank
      ( B ) CLONE: GI 1072118

( x i ) SEQUENCE DESCRIPTION: SEQ ID NO:3:

```
Met  Glu  Gly  Gly  Ala  Tyr  Gly  Ala  Gly  Lys  Ala  Gly  Asp  Pro  Tyr  Thr
 1                  5                      10                       15

Leu  Val  Arg  Gln  Pro  His  Thr  Ile  Leu  Arg  Val  Val  Ser  Trp  Val  Phe
               20                      25                      30

Ser  Ile  Val  Val  Phe  Gly  Ser  Ile  Val  Asn  Glu  Gly  Tyr  Leu  Asn  Asn
               35                      40                      45

Pro  Glu  Glu  Glu  Glu  Glu  Phe  Cys  Ile  Tyr  Asn  Arg  Asn  Pro  Asn  Ala
          50                      55                      60

Cys  Ser  Tyr  Gly  Val  Thr  Val  Gly  Val  Leu  Ala  Phe  Leu  Thr  Cys  Leu
65                      70                      75                       80

Val  Tyr  Leu  Ala  Leu  Asp  Val  Tyr  Phe  Pro  Gln  Ile  Ser  Ser  Val  Lys
                    85                      90                      95

Asp  Arg  Lys  Lys  Ala  Val  Leu  Ser  Asp  Ile  Gly  Val  Ser  Ala  Phe  Trp
               100                     105                     110

Ala  Phe  Phe  Trp  Phe  Val  Gly  Phe  Cys  Phe  Leu  Ala  Asn  Gln  Trp  Gln
          115                     120                     125

Val  Ser  Lys  Pro  Lys  Asp  Asn  Pro  Leu  Asn  Glu  Gly  Thr  Asp  Ala  Ala
     130                     135                     140

Arg  Ala  Ala  Ile  Ala  Phe  Ser  Phe  Phe  Ser  Ile  Phe  Thr  Trp  Ala  Gly
145                     150                     155                     160

Gln  Ala  Val  Leu  Ala  Phe  Gln  Arg  Tyr  Gln  Ile  Gly  Ala  Asp  Ser  Ala
                    165                     170                     175

Leu  Phe  Cys  Gln  Asp  Tyr  Met  Asp  Pro  Ser  Gln  Asp  Ser  Ser  Met  Pro
               180                     185                     190

Tyr  Ala  Pro  Tyr  Val  Glu  Pro  Ser  Ala  Gly  Ser  Asp  Pro  Thr  Gly  Met
          195                     200                     205

Gly  Gly  Thr  Tyr  Gln  His  Pro  Ala  Asn  Ala  Phe  Asp  Ala  Glu  Pro  Gln
     210                     215                     220

Gly  Tyr  Gln  Ser  Gln  Gly  Tyr
225                     230
```

( 2 ) INFORMATION FOR SEQ ID NO:4:

( i ) SEQUENCE CHARACTERISTICS:
        ( A ) LENGTH: 296 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: GI 899301

( x i ) SEQUENCE DESCRIPTION: SEQ ID NO:4:

```
Gln Phe Arg Val Val Lys Glu Pro Leu Gly Phe Val Lys Val Leu Gln
 1               5                  10                  15
Trp Val Phe Ala Ile Phe Ala Phe Ala Thr Cys Gly Ser Tyr Ser Gly
                20                  25                  30
Glu Leu Gln Leu Ser Val Asp Cys Ala Asn Lys Thr Glu Ser Asp Leu
                35                  40                  45
Ser Ile Glu Val Glu Phe Glu Tyr Pro Phe Arg Leu His Gln Val Tyr
        50                  55                  60
Phe Asp Ala Pro Thr Cys Arg Gly Gly Thr Thr Lys Val Phe Leu Val
 65                  70                  75                  80
Gly Asp Tyr Ser Ser Ser Ala Glu Phe Phe Val Thr Val Ala Val Phe
                85                  90                  95
Ala Phe Leu Tyr Ser Met Gly Ala Leu Ala Thr Tyr Ile Phe Leu Gln
                100                 105                 110
Asn Lys Tyr Arg Glu Asn Asn Lys Gly Pro Met Leu Asp Phe Leu Ala
        115                 120                 125
Thr Ala Val Phe Ala Phe Met Trp Leu Val Ser Ser Ser Ala Trp Ala
    130                 135                 140
Lys Gly Leu Ser Asp Val Lys Met Ala Thr Asp Pro Glu Asn Ile Ile
145                 150                 155                 160
Lys Glu Met Pro Val Cys Arg Gln Thr Gly Asn Thr Cys Lys Glu Leu
                165                 170                 175
Arg Asp Pro Val Thr Ser Gly Leu Asn Thr Ser Val Val Phe Gly Phe
                180                 185                 190
Leu Asn Leu Val Leu Trp Val Gly Asn Leu Trp Phe Val Phe Lys Glu
        195                 200                 205
Thr Gly Trp Ala Ala Pro Phe Leu Arg Ala Pro Pro Gly Ala Pro Glu
    210                 215                 220
Lys Gln Pro Ala Pro Gly Asp Ala Tyr Gly Asp Ala Gly Tyr Gly Gln
225                 230                 235                 240
Gly Pro Gly Gly Tyr Gly Pro Gln Asp Ser Tyr Gly Pro Gln Gly Gly
                245                 250                 255
Tyr Gln Pro Asp Tyr Gly Gln Pro Ala Gly Ser Gly Gly Ser Gly Tyr
                260                 265                 270
Gly Pro Gln Gly Asp Tyr Gly Gln Gln Gly Tyr Gly Pro Gln Gly Ala
        275                 280                 285
Pro Thr Ser Phe Ser Asn Gln Met
    290                 295
```

( 2 ) INFORMATION FOR SEQ ID NO:5:

( i ) SEQUENCE CHARACTERISTICS:
        ( A ) LENGTH: 232 base pairs
        ( B ) TYPE: nucleic acid
        ( C ) STRANDEDNESS: single ( D ) TOPOLOGY: linear ( i i ) MOLECULE TYPE: cDNA ( v i i ) IMMEDIATE SOURCE:
    ( A ) LIBRARY: TMLR2DT01
    ( B ) CLONE: 392250

( x i ) SEQUENCE DESCRIPTION: SEQ ID NO:5:

```
GCGGCCAAGG  CGGGCGGCTC  CTTCGACCTG  CGGCGCTTCC  TGACGCAGCC  GCAGGTGGTG    60
GCGCGCGCCG  TGTGCTTGGT  CTTCGNCTTG  ATCGTGTTCT  CCTGCATCTA  TGGTGAGGGC   120
TACAGCAATG  CCCACGAGTC  TAAGCAGATG  TACTGCGTGT  TCAACCGCAA  CGAGGATGCC   180
TGCCGCTATG  GCAGTGCCAT  CGGGGTGCTG  GCCTTCCTGG  CCTCGGCTTT  CT           232
```

( 2 ) INFORMATION FOR SEQ ID NO:6:

( i ) SEQUENCE CHARACTERISTICS:
        ( A ) LENGTH: 272 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: MMLR2DT01
        ( B ) CLONE: 476266

( x i ) SEQUENCE DESCRIPTION: SEQ ID NO:6:

```
GGCGGCGACG  GCGACATGGA  GAGCGGGGCC  TACGGCGCGG  CCAAGGCGGG  CGGNTNCTTC    60
GACCTGCGGC  GNTTCCTGAC  GNAGCCGCAG  GTGGTGGCGC  GCGCCGTGTG  CTTGGTCTTC   120
GCCTTGATCG  TGTTCTCCTG  CATCTATGGT  GAGGGCTACA  GCAATGCCCA  CGAGTCTAAG   180
CAGATGTACT  GCGTGTTCAA  CCGNAACGAG  GATGCCTGCC  GNTATGGCAG  TGCCATCGGG   240
GTGCTGGCCT  TNCTGGNCTN  GGNCTTCTTN  TT                                  272
```

( 2 ) INFORMATION FOR SEQ ID NO:7:

( i ) SEQUENCE CHARACTERISTICS:
        ( A ) LENGTH: 265 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: COLNNOT01
        ( B ) CLONE: 608493

( x i ) SEQUENCE DESCRIPTION: SEQ ID NO:7:

```
AGCGGGGCCT  ACGGCGCGGC  CAAGGCGGGC  GGCTCCTTCG  ACCTGCGGCG  CTTCCTGACG    60
CAGCCGCAGG  TGGTGGCGCG  CGCCGTGTGC  TTNGTCTTCG  CCTTGATCGT  NTTCTCCTGC   120
ATCTATGGTG  AGGGCTACAG  CAATGCCCAC  GAGTCTAAGC  AGATGTACTG  CGTGTTCAAC   180
CGCAACGAGG  ATGCCTGCCG  CTATGGCAGT  GCCATCGGGG  TGCTGGCCTT  CCTGGCCTCG   240
GCCTTNTTNT  TGGTGGTCGA  CGCGT                                           265
```

( 2 ) INFORMATION FOR SEQ ID NO:8:

( i ) SEQUENCE CHARACTERISTICS:
        ( A ) LENGTH: 192 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
    ( A ) LIBRARY: LUNGTUT02
    ( B ) CLONE: 693335

( x i ) SEQUENCE DESCRIPTION: SEQ ID NO:8:

| | | | | | |
|---|---|---|---|---|---|
| CCGCGGCCAA | GGCGGGCGGC | TCCTTCGACC | TGCGGCGCTT | NCTGACGNAG | CCGCAGTGGT | 60 |
| GGCGCGCGCC | GTGTGCTTGG | TCTTCGCCTT | GATCGTGTTC | TCCTGCATNT | ATGGTGAGGG | 120 |
| CTACAGCAAT | GCCCACGAGT | CTAAGCAGAT | GTACTGCGTG | TTCAACCGCA | ACGAGGATGN | 180 |
| CTGCCGCTAT | GG | | | | | 192 |

( 2 ) INFORMATION FOR SEQ ID NO:9:

( i ) SEQUENCE CHARACTERISTICS:
        ( A ) LENGTH: 220 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
    ( A ) LIBRARY: SYNORAT03
    ( B ) CLONE: 695983

( x i ) SEQUENCE DESCRIPTION: SEQ ID NO:9:

| | | | | | |
|---|---|---|---|---|---|
| GGCGCGGCCA | AGGCGGGCGG | NTCCTTCGAC | CTNCGGCGNT | TNCTGACGNA | GCCGCANGTG | 60 |
| GTGGCGCGCG | CCGTGTGCTT | GGTCTTCGNC | TTGATCGTGT | TCTTCTGCAT | CTATGGTGAG | 120 |
| GGCTACAGCA | ATGNCCACGA | GTCTAAGCAG | ATGTACTNCG | TGTTCAANCG | CAACGAGGAT | 180 |
| GNCTGCCGCT | ATGGCAGTGC | CATCGGGGTG | CTGGNCTTTC | | | 220 |

( 2 ) INFORMATION FOR SEQ ID NO:10:

( i ) SEQUENCE CHARACTERISTICS:
        ( A ) LENGTH: 230 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
    ( A ) LIBRARY: BRAITUT02
    ( B ) CLONE: 754306

( x i ) SEQUENCE DESCRIPTION: SEQ ID NO:10:

| | | | | | |
|---|---|---|---|---|---|
| GAGAGCGGGG | CCTACGGCGC | GGCCAAGGCG | GGCGGCTCCT | TCGACCTGCG | GCGCTTCCTG | 60 |
| ACGCAGCCGC | AGTGGTGGCG | CGCGCCGTGT | GCTTGGTCTT | CGCCTTGATC | GTGTTCTCCT | 120 |
| GCATCTATGG | TGAGGGCTAC | AGCAATGCCC | ACGAGTCTAA | GCAGATGTAC | TGCGTGTTCA | 180 |
| ACCGCAACGA | GGATGCCTGC | CGCTATGGCA | GTGCCATCGG | GGTGCTGGCC | | 230 |

( 2 ) INFORMATION FOR SEQ ID NO:11:

( i ) SEQUENCE CHARACTERISTICS:
        ( A ) LENGTH: 296 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
    ( A ) LIBRARY: LUNGNOT04

(B) CLONE: 809604

(x i) SEQUENCE DESCRIPTION: SEQ ID NO:11:

| | | | | | |
|---|---|---|---|---|---|
| GCGGCAGCGG | CGGCGACGGC | GACATGGAGA | GCGGGGCCTA | CGGCGCGGCC | AAGGCGGGCG | 60
| GCTNCTTCGA | CCTGCGGCGC | TTCCTGACGC | AGCCGCAGTG | GTGGCGCGCG | CCGTGTGNTT | 120
| GGTCTTGGGC | TTGATCGTGT | TCTCCTGCAT | CTATGGTGAG | GGCTACAGCA | ATGCCCACGA | 180
| GTCTAAGCAG | ATGTACTGCG | TGTTCAACCG | CAACGAGGAT | GCCTGCCGCT | ATGGCAGTGC | 240
| CATCGGGGTG | CTGGCCTTNC | TGGCCTCGGC | CTTNTTNTTG | GTGGTCGACG | CGTATT | 296

(2) INFORMATION FOR SEQ ID NO:12:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: LUNGAST01
        (B) CLONE: 868416

(x i) SEQUENCE DESCRIPTION: SEQ ID NO:12:

| | | | | | |
|---|---|---|---|---|---|
| CGACATGGAG | AGCGGGGCCT | ACGGCGCGGC | CAAGGCGGGC | GGCTCCTTCG | ACCTGCGGCG | 60
| NTTNCTGACG | NAGCCGCAGG | TGGTGGCGCG | CGCCGTGTGC | TTGGTCTTCG | NCTTGATCGT | 120
| GTTCTCCTGC | ATCTATGGTG | AGGGCTACAG | CAATGCCCAC | GAGTCTAAGC | AGATGTACTG | 180
| CGTGTTCAAC | CGCAACGAGG | ATGCTGCCGT | ATGGCAGTGC | CATCGGGGTG | CTGGCTTCTG | 240
| GCTNGGCTTT | TTTGGTGGCG | CGGGATTTCC | CCAANNAGAA | CGCATNCCGA | AGACTGNATT | 300
| GNNCTNTTTT | AGTTTGNCTC | TTGTTGTGTT | GTCNACAAC | | | 339